(12) United States Patent
Hartwell et al.

(10) Patent No.: US 11,793,924 B2
(45) Date of Patent: Oct. 24, 2023

(54) SYSTEMS AND METHODS FOR DELIVERING PRESCRIBED WOUND THERAPY

(71) Applicant: T.J.Smith and Nephew, Limited, Hull (GB)

(72) Inventors: Edward Yerbury Hartwell, Hull (GB); Felix Clarence Quintanar, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 43 days.

(21) Appl. No.: 17/416,385

(22) PCT Filed: Dec. 11, 2019

(86) PCT No.: PCT/EP2019/084611
§ 371 (c)(1),
(2) Date: Jun. 18, 2021

(87) PCT Pub. No.: WO2020/126735
PCT Pub. Date: Jun. 25, 2020

(65) Prior Publication Data
US 2021/0379272 A1    Dec. 9, 2021

(30) Foreign Application Priority Data
Dec. 19, 2018    (GB) .................................... 1820668

(51) Int. Cl.
*A61M 1/00*    (2006.01)
*G16H 20/40*    (2018.01)

(52) U.S. Cl.
CPC .......... *A61M 1/90* (2021.05); *A61M 2205/18* (2013.01); *A61M 2205/35* (2013.01);
(Continued)

(58) Field of Classification Search
CPC ................ A61M 1/90; A61M 2205/18; A61M 2205/3553; A61M 2205/502;
(Continued)

(56) References Cited

U.S. PATENT DOCUMENTS

| | | |
|---|---|---|
| 695,270 A | 3/1902 | Beringer |
| 3,194,239 A | 7/1965 | Sullivan et al. |

(Continued)

FOREIGN PATENT DOCUMENTS

| | | |
|---|---|---|
| CN | 102961815 A | 3/2013 |
| CN | 104721892 A | 6/2015 |

(Continued)

OTHER PUBLICATIONS

International Preliminary Report on Patentability for Application No. PCT/EP2019/084611, dated Jul. 1, 2021, 9 pages.

(Continued)

*Primary Examiner* — Erich G Herbermann
*Assistant Examiner* — Peter Daniel Smith
(74) *Attorney, Agent, or Firm* — Knobbe, Martens Olson & Bear, LLP

(57) ABSTRACT

Embodiments of delivering reduced pressure wound therapy are disclosed. In some embodiments, a system includes a reduced pressure wound therapy device and a remote computer. The device can be configured to apply reduced pressure to a wound of a patient according to a default reduced pressure therapy prescription. The device can be configured to monitor usage data and transmit the usage data to the remove computer for determining compliance with a reduced therapy prescription. In some cases, non-compliance can be determined due to change of the prescription from the default prescription to a prescription more suitable (Continued)

for treating the wound. A non-compliance notification can be transmitted to the device. The device settings can be updated to the current prescription.

17 Claims, 6 Drawing Sheets

(52) U.S. Cl.
CPC .............. *A61M 2205/3553* (2013.01); *A61M 2205/502* (2013.01); *G16H 20/40* (2018.01)

(58) Field of Classification Search
CPC ...... A61M 2205/35; A61M 2205/3546; G16H 20/10; G16H 40/40; G16H 40/60; G16H 20/40; G16H 40/67; G16H 20/60
See application file for complete search history.

(56) References Cited

U.S. PATENT DOCUMENTS

| | | | |
|---|---|---|---|
| 4,832,299 | A | 5/1989 | Gorton et al. |
| 5,219,428 | A | 6/1993 | Stern |
| 5,473,536 | A | 12/1995 | Wimmer |
| 5,960,403 | A | 9/1999 | Brown |
| 6,055,506 | A | 4/2000 | Frasca et al. |
| 6,336,900 | B1 | 1/2002 | Alleckson et al. |
| 6,353,445 | B1 | 3/2002 | Babula et al. |
| 6,375,614 | B1 | 4/2002 | Braun et al. |
| 6,385,622 | B2 | 5/2002 | Bouve et al. |
| 6,406,426 | B1 | 6/2002 | Reuss et al. |
| 6,434,572 | B2 | 8/2002 | Derzay et al. |
| 6,460,041 | B2 | 10/2002 | Lloyd |
| 6,574,518 | B1 | 6/2003 | Lounsberry et al. |
| 6,640,145 | B2 | 10/2003 | Hoffberg et al. |
| 6,640,246 | B1 | 10/2003 | Gary et al. |
| 6,675,131 | B2 | 1/2004 | Hahn |
| 6,681,003 | B2 | 1/2004 | Linder et al. |
| 6,723,046 | B2 | 4/2004 | Lichtenstein et al. |
| 6,730,024 | B2 | 5/2004 | Freyre et al. |
| 6,747,556 | B2 | 6/2004 | Medema et al. |
| 6,779,024 | B2 | 8/2004 | DeLaHuerga |
| 6,782,285 | B2 | 8/2004 | Birkenbach et al. |
| 6,856,825 | B2 | 2/2005 | Hahn |
| 6,868,528 | B2 | 3/2005 | Roberts |
| 6,871,211 | B2 | 3/2005 | Labounty et al. |
| 6,909,974 | B2 | 6/2005 | Yung et al. |
| 6,912,481 | B2 | 6/2005 | Breunissen et al. |
| 6,961,731 | B2 | 11/2005 | Holbrook |
| 7,004,915 | B2 | 2/2006 | Boynton et al. |
| 7,022,113 | B2 | 4/2006 | Lockwood et al. |
| 7,051,012 | B2 | 5/2006 | Cole et al. |
| 7,062,251 | B2 | 6/2006 | Birkett et al. |
| 7,066,883 | B2 | 6/2006 | Schmidt et al. |
| 7,103,578 | B2 | 9/2006 | Beck et al. |
| 7,108,683 | B2 | 9/2006 | Zamierowski |
| 7,120,488 | B2 | 10/2006 | Nova et al. |
| 7,133,869 | B2 | 11/2006 | Bryan et al. |
| 7,167,858 | B2 | 1/2007 | Naeymi-Rad et al. |
| 7,212,829 | B1 | 5/2007 | Lau et al. |
| 7,264,591 | B2 | 9/2007 | Brown |
| 7,300,418 | B2 | 11/2007 | Zaleski |
| 7,304,573 | B2 | 12/2007 | Postma |
| 7,311,665 | B2 | 12/2007 | Hawthorne et al. |
| 7,333,002 | B2 | 2/2008 | Bixler et al. |
| 7,353,179 | B2 | 4/2008 | Ott et al. |
| 7,384,267 | B1 | 6/2008 | Franks et al. |
| 7,430,598 | B2 | 9/2008 | Raden et al. |
| 7,430,608 | B2 | 9/2008 | Noonan et al. |
| 7,438,705 | B2 | 10/2008 | Karpowicz et al. |
| 7,451,002 | B2 | 11/2008 | Choubey |
| 7,457,804 | B2 | 11/2008 | Uber et al. |
| 7,460,872 | B2 | 12/2008 | Millard et al. |
| 7,534,240 | B1 | 5/2009 | Johnson |
| 7,598,855 | B2 | 10/2009 | Scalisi et al. |
| 7,608,066 | B2 | 10/2009 | Vogel |
| 7,627,334 | B2 | 12/2009 | Cohen et al. |
| 7,649,449 | B2 | 1/2010 | Fenske et al. |
| 7,671,733 | B2 | 3/2010 | McNeal et al. |
| 7,684,999 | B2 | 3/2010 | Brown |
| 7,698,156 | B2 | 4/2010 | Martucci et al. |
| 7,734,764 | B2 | 6/2010 | Weiner et al. |
| 7,749,164 | B2 | 7/2010 | Davis |
| 7,758,555 | B2 | 7/2010 | Kelch et al. |
| 7,779,153 | B2 | 8/2010 | Van den Heuvel et al. |
| 7,789,828 | B2 | 9/2010 | Clapp |
| 7,794,438 | B2 | 9/2010 | Henley et al. |
| 7,827,148 | B2 | 11/2010 | Mori et al. |
| 7,865,375 | B2 | 1/2011 | Lancaster et al. |
| 7,889,069 | B2 | 2/2011 | Fifolt et al. |
| 7,890,887 | B1 | 2/2011 | Linardos et al. |
| 7,912,823 | B2 | 3/2011 | Ferrari et al. |
| 7,925,603 | B1 | 4/2011 | Laidig et al. |
| 7,933,817 | B2 | 4/2011 | Radl et al. |
| 7,976,519 | B2 | 7/2011 | Bubb et al. |
| 7,981,098 | B2 | 7/2011 | Boehringer et al. |
| 7,988,850 | B2 | 8/2011 | Roncadi et al. |
| 8,015,443 | B2 | 9/2011 | Adachi |
| 8,015,972 | B2 | 9/2011 | Pirzada |
| 8,019,618 | B2 | 9/2011 | Brown |
| 8,036,925 | B2 | 10/2011 | Choubey |
| 8,054,950 | B1 | 11/2011 | Hung et al. |
| 8,069,057 | B2 | 11/2011 | Choubey et al. |
| 8,094,009 | B2 | 1/2012 | Allen et al. |
| 8,126,735 | B2 | 2/2012 | Dicks et al. |
| 8,130,095 | B2 | 3/2012 | Allen et al. |
| 8,131,472 | B2 | 3/2012 | Chow et al. |
| 8,180,750 | B2 | 5/2012 | Wilmering et al. |
| 8,190,445 | B2 | 5/2012 | Kuth et al. |
| 8,190,448 | B2 | 5/2012 | Bajars et al. |
| 8,228,188 | B2 | 7/2012 | Key et al. |
| 8,246,606 | B2 | 8/2012 | Stevenson et al. |
| 8,249,894 | B2 | 8/2012 | Brown |
| 8,255,241 | B2 | 8/2012 | Cafer |
| 8,260,630 | B2 | 9/2012 | Brown |
| 8,280,682 | B2 | 10/2012 | Vock et al. |
| 8,284,046 | B2 | 10/2012 | Allen et al. |
| 8,290,792 | B2 | 10/2012 | Sekura |
| 8,291,337 | B2 | 10/2012 | Gannin et al. |
| 8,332,233 | B2 | 12/2012 | Ott et al. |
| 8,332,236 | B2 | 12/2012 | Yurko et al. |
| 8,334,768 | B2 | 12/2012 | Eaton et al. |
| 8,360,975 | B1 | 1/2013 | Schwieterman et al. |
| 8,361,056 | B2 | 1/2013 | Wood et al. |
| 8,400,295 | B1 | 3/2013 | Khaira |
| 8,422,377 | B2 | 4/2013 | Weiner et al. |
| 8,424,517 | B2 | 4/2013 | Sutherland et al. |
| 8,436,871 | B2 | 5/2013 | Alberte |
| 8,439,882 | B2 | 5/2013 | Kelch |
| 8,457,740 | B2 | 6/2013 | Osche |
| 8,480,641 | B2 | 7/2013 | Jacobs |
| 8,515,776 | B2 | 8/2013 | Schoenberg |
| 8,532,764 | B2 | 9/2013 | Duke |
| 8,540,688 | B2 | 9/2013 | Eckstein et al. |
| 8,545,483 | B2 | 10/2013 | Schwabe et al. |
| 8,554,195 | B2 | 10/2013 | Rao |
| 8,554,902 | B2 | 10/2013 | Ebert et al. |
| 8,558,964 | B2 | 10/2013 | Bedingfield |
| 8,560,082 | B2 | 10/2013 | Wei |
| 8,577,694 | B2 | 11/2013 | Kanaan |
| 8,595,553 | B2 | 11/2013 | Goertler et al. |
| 8,600,777 | B2 | 12/2013 | Schoenberg et al. |
| 8,626,342 | B2 | 1/2014 | Williams et al. |
| 8,626,526 | B2 | 1/2014 | Lemke et al. |
| 8,630,660 | B2 | 1/2014 | Ray et al. |
| 8,632,485 | B2 | 1/2014 | Schlaeper et al. |
| 8,641,693 | B2 | 2/2014 | Locke et al. |
| 8,659,420 | B2 | 2/2014 | Salvat et al. |
| 8,676,597 | B2 | 3/2014 | Buehler et al. |
| 8,689,008 | B2 | 4/2014 | Rangadass et al. |
| 8,694,600 | B2 | 4/2014 | Gaines et al. |
| 8,706,537 | B1 | 4/2014 | Young et al. |
| 8,725,528 | B2 | 5/2014 | Locke et al. |
| 8,756,078 | B2 | 6/2014 | Collins et al. |

(56) References Cited

U.S. PATENT DOCUMENTS

| | | |
|---|---|---|
| 8,757,485 B2 | 6/2014 | Drees et al. |
| 8,758,315 B2 | 6/2014 | Chen et al. |
| 8,768,441 B2 | 7/2014 | De Zwart et al. |
| 8,769,625 B2 | 7/2014 | Wang et al. |
| 8,781,847 B2 | 7/2014 | Simms et al. |
| 8,795,171 B2 | 8/2014 | Adamczyk |
| 8,795,244 B2 | 8/2014 | Randolph et al. |
| 8,838,136 B2 | 9/2014 | Carnes et al. |
| 8,862,393 B2 | 10/2014 | Zhou et al. |
| 8,868,794 B2 | 10/2014 | Masoud et al. |
| 8,874,035 B2 | 10/2014 | Sherman et al. |
| 8,887,100 B1 | 11/2014 | Cook et al. |
| 8,890,656 B2 | 11/2014 | Pendse |
| 8,897,198 B2 | 11/2014 | Gaines et al. |
| 8,902,278 B2 | 12/2014 | Pinter et al. |
| 8,905,959 B2 | 12/2014 | Basaglia |
| 8,909,595 B2 | 12/2014 | Gandy et al. |
| 8,912,897 B2 | 12/2014 | Carnes |
| 8,922,377 B2 | 12/2014 | Carnes |
| 8,945,073 B2 | 2/2015 | Croizat et al. |
| 8,947,237 B2 | 2/2015 | Margon et al. |
| 8,978,026 B2 | 3/2015 | Charlton et al. |
| 8,996,393 B2 | 3/2015 | Sobie |
| 9,047,648 B1 | 6/2015 | Lekutai et al. |
| 9,058,634 B2 | 6/2015 | Buan et al. |
| 9,081,885 B2 | 7/2015 | Bangera et al. |
| 9,087,141 B2 | 7/2015 | Huang et al. |
| 9,092,705 B2 | 7/2015 | Zhuang |
| 9,098,114 B2 | 8/2015 | Potter et al. |
| 9,105,006 B2 | 8/2015 | Williamson |
| 9,114,054 B2 | 8/2015 | Bennett |
| 9,117,012 B2 | 8/2015 | Basaglia |
| 9,135,398 B2 | 9/2015 | Kaib et al. |
| 9,141,270 B1 | 9/2015 | Stuart et al. |
| 9,159,148 B2 | 10/2015 | Boyer et al. |
| 9,215,075 B1 | 12/2015 | Poltorak |
| 9,215,516 B2 | 12/2015 | Carnes et al. |
| 9,215,581 B2 | 12/2015 | Julian et al. |
| 9,230,420 B2 | 1/2016 | Lee et al. |
| 9,268,827 B2 | 2/2016 | Fernandez |
| 9,286,443 B2 | 3/2016 | Ford et al. |
| 9,323,893 B2 | 4/2016 | Berry et al. |
| 9,332,363 B2 | 5/2016 | Jain et al. |
| 9,338,819 B2 | 5/2016 | Meng et al. |
| 9,427,159 B2 | 8/2016 | Chang |
| 9,436,645 B2 | 9/2016 | Al-Ali et al. |
| 9,436,800 B2 | 9/2016 | Forrester |
| 9,439,584 B1 | 9/2016 | De Vries et al. |
| 9,460,431 B2 | 10/2016 | Curry |
| 9,474,679 B2 | 10/2016 | Locke et al. |
| 9,483,614 B2 | 11/2016 | Ash et al. |
| 9,539,373 B2 | 1/2017 | Jones et al. |
| 9,545,466 B2 | 1/2017 | Locke et al. |
| 9,558,331 B2 | 1/2017 | Orona et al. |
| 9,585,565 B2 | 3/2017 | Carnes |
| 9,589,247 B2 | 3/2017 | Bolene et al. |
| 9,602,952 B2 | 3/2017 | Kang et al. |
| 9,629,986 B2 | 4/2017 | Patel et al. |
| 9,658,066 B2 | 5/2017 | Yuen et al. |
| 9,662,438 B2 | 5/2017 | Kamen et al. |
| 9,687,618 B2 | 6/2017 | Steinhauer et al. |
| 9,693,691 B2 | 7/2017 | Johnson |
| 9,700,462 B2 | 7/2017 | DeBusk et al. |
| 9,716,757 B2 | 7/2017 | Fernandes |
| 9,740,825 B2 | 8/2017 | Sansale et al. |
| 9,741,084 B2 | 8/2017 | Holmes et al. |
| 9,787,842 B1 | 10/2017 | Brooksby et al. |
| 9,792,660 B2 | 10/2017 | Cannon et al. |
| 9,817,948 B2 | 11/2017 | Swank |
| 9,818,164 B2 | 11/2017 | Nolte et al. |
| 9,838,645 B2 | 12/2017 | Hyde et al. |
| 9,878,081 B2 | 1/2018 | Leiendecker et al. |
| 9,905,123 B2 | 2/2018 | Lawhorn |
| 9,928,478 B2 | 3/2018 | Ragusky et al. |
| 9,974,492 B1 | 5/2018 | Dicks et al. |
| 9,990,466 B2 | 6/2018 | DeBusk et al. |
| 9,996,681 B2 | 6/2018 | Suarez et al. |
| 10,049,346 B2 | 8/2018 | Jensen et al. |
| 10,061,894 B2 | 8/2018 | Sethumadhavan et al. |
| 10,095,649 B2 | 10/2018 | Joshua et al. |
| 10,127,357 B2 | 11/2018 | Whiting et al. |
| 10,152,575 B2 | 12/2018 | Sexton et al. |
| 10,173,008 B2 | 1/2019 | Simpson et al. |
| 10,185,834 B2 | 1/2019 | Adam et al. |
| 10,207,031 B2 | 2/2019 | Toth |
| 10,328,188 B2 | 6/2019 | Deutsch et al. |
| 2002/0087360 A1 | 7/2002 | Pettit |
| 2002/0128804 A1 | 9/2002 | Geva |
| 2002/0128869 A1 | 9/2002 | Kuth |
| 2002/0135336 A1 | 9/2002 | Zhou et al. |
| 2002/0161317 A1* | 10/2002 | Risk ................ A61M 1/0058 602/2 |
| 2002/0177757 A1 | 11/2002 | Britton |
| 2002/0184055 A1 | 12/2002 | Naghavi et al. |
| 2003/0009244 A1 | 1/2003 | Engleson et al. |
| 2003/0018736 A1 | 1/2003 | Christ et al. |
| 2003/0105649 A1 | 6/2003 | Sheiner et al. |
| 2003/0182158 A1 | 9/2003 | Son |
| 2003/0221687 A1 | 12/2003 | Kaigler |
| 2003/0229518 A1 | 12/2003 | Abraham-Fuchs et al. |
| 2004/0006319 A1* | 1/2004 | Lina .................. A61M 1/74 604/304 |
| 2004/0006492 A1 | 1/2004 | Watanabe |
| 2004/0054775 A1 | 3/2004 | Poliac et al. |
| 2004/0078223 A1 | 4/2004 | Sacco et al. |
| 2004/0127774 A1* | 7/2004 | Moore ............... A61N 1/3925 600/300 |
| 2004/0143458 A1 | 7/2004 | Pulkkinen et al. |
| 2004/0167802 A1 | 8/2004 | Takada et al. |
| 2004/0167804 A1 | 8/2004 | Simpson et al. |
| 2004/0172301 A1 | 9/2004 | Mihai et al. |
| 2004/0181433 A1 | 9/2004 | Blair |
| 2004/0187871 A1* | 9/2004 | Kimmel ............ A61B 5/4833 128/204.23 |
| 2004/0193449 A1 | 9/2004 | Wildman et al. |
| 2004/0204962 A1 | 10/2004 | Howser et al. |
| 2005/0033124 A1 | 2/2005 | Kelly et al. |
| 2005/0055225 A1 | 3/2005 | Mehl |
| 2005/0055242 A1 | 3/2005 | Bello et al. |
| 2005/0055244 A1 | 3/2005 | Mullan et al. |
| 2005/0060211 A1 | 3/2005 | Xiao et al. |
| 2005/0065817 A1 | 3/2005 | Mihai et al. |
| 2005/0097200 A1 | 5/2005 | Denning, Jr. et al. |
| 2005/0102167 A1 | 5/2005 | Kapoor |
| 2005/0108046 A1 | 5/2005 | Craft |
| 2005/0108057 A1 | 5/2005 | Cohen et al. |
| 2005/0114176 A1 | 5/2005 | Dominick et al. |
| 2005/0119914 A1 | 6/2005 | Batch |
| 2005/0222873 A1 | 10/2005 | Nephin et al. |
| 2005/0240111 A1 | 10/2005 | Chung |
| 2005/0283382 A1 | 12/2005 | Donoghue et al. |
| 2006/0004604 A1 | 1/2006 | White |
| 2006/0064323 A1 | 3/2006 | Alleckson et al. |
| 2006/0085393 A1 | 4/2006 | Modesitt |
| 2006/0089539 A1 | 4/2006 | Miodownik et al. |
| 2006/0095853 A1 | 5/2006 | Amyot et al. |
| 2006/0155584 A1 | 7/2006 | Aggarwal |
| 2006/0161460 A1 | 7/2006 | Smitherman et al. |
| 2006/0190130 A1 | 8/2006 | Fedor et al. |
| 2006/0195843 A1 | 8/2006 | Hall |
| 2006/0224051 A1 | 10/2006 | Teller et al. |
| 2006/0246922 A1 | 11/2006 | Gasbarro et al. |
| 2007/0136099 A1 | 6/2007 | Neligh et al. |
| 2007/0156456 A1 | 7/2007 | McGillin et al. |
| 2007/0197881 A1 | 8/2007 | Wolf et al. |
| 2007/0219826 A1 | 9/2007 | Brodsky et al. |
| 2007/0255116 A1 | 11/2007 | Mehta et al. |
| 2007/0271298 A1 | 11/2007 | Juang et al. |
| 2008/0009681 A1 | 1/2008 | Al Hussiny |
| 2008/0086357 A1 | 4/2008 | Choubey et al. |
| 2008/0091659 A1 | 4/2008 | McFaul |
| 2008/0119705 A1 | 5/2008 | Patel et al. |
| 2008/0126126 A1 | 5/2008 | Ballai |
| 2008/0140160 A1 | 6/2008 | Goetz et al. |

(56) References Cited

U.S. PATENT DOCUMENTS

| | | |
|---|---|---|
| 2008/0167534 A1 | 7/2008 | Young et al. |
| 2008/0177579 A1 | 7/2008 | Dehaan |
| 2008/0221396 A1 | 9/2008 | Garces et al. |
| 2008/0242945 A1 | 10/2008 | Gugliotti et al. |
| 2008/0312953 A1 | 12/2008 | Claus |
| 2009/0033482 A1* | 2/2009 | Hayter ............... G16H 40/40 340/691.5 |
| 2009/0037220 A1 | 2/2009 | Chambers et al. |
| 2009/0048492 A1 | 2/2009 | Rantala et al. |
| 2009/0048865 A1 | 2/2009 | Breazeale, Jr. |
| 2009/0082641 A1* | 3/2009 | Giftakis ............... G16H 40/63 600/300 |
| 2009/0097623 A1 | 4/2009 | Bharadwaj |
| 2009/0099866 A1 | 4/2009 | Newman |
| 2009/0099867 A1 | 4/2009 | Newman |
| 2009/0115663 A1 | 5/2009 | Brown et al. |
| 2009/0118591 A1 | 5/2009 | Kim et al. |
| 2009/0125331 A1 | 5/2009 | Pamsgaard et al. |
| 2009/0136909 A1 | 5/2009 | Asukai et al. |
| 2009/0144091 A1 | 6/2009 | Rago |
| 2009/0157429 A1 | 6/2009 | Lee et al. |
| 2009/0163774 A1 | 6/2009 | Thatha et al. |
| 2009/0171166 A1 | 7/2009 | Amundson et al. |
| 2009/0177495 A1 | 7/2009 | Abousy et al. |
| 2009/0187424 A1 | 7/2009 | Grabowski |
| 2009/0204434 A1 | 8/2009 | Breazeale, Jr. |
| 2009/0204435 A1 | 8/2009 | Gale |
| 2009/0205042 A1 | 8/2009 | Zhou et al. |
| 2009/0224889 A1 | 9/2009 | Aggarwal et al. |
| 2009/0270833 A1 | 10/2009 | DeBelser et al. |
| 2009/0281822 A1 | 11/2009 | Warner et al. |
| 2009/0281830 A1 | 11/2009 | McNames et al. |
| 2009/0281867 A1 | 11/2009 | Sievenpiper et al. |
| 2009/0299306 A1* | 12/2009 | Buan ............... A61M 1/74 604/319 |
| 2009/0326339 A1 | 12/2009 | Horvitz |
| 2009/0327102 A1 | 12/2009 | Maniar et al. |
| 2010/0001838 A1 | 1/2010 | Miodownik et al. |
| 2010/0017471 A1 | 1/2010 | Brown et al. |
| 2010/0022848 A1 | 1/2010 | Lee et al. |
| 2010/0022990 A1 | 1/2010 | Karpowicz et al. |
| 2010/0030302 A1 | 2/2010 | Blowers et al. |
| 2010/0036333 A1 | 2/2010 | Schenk, III et al. |
| 2010/0042059 A1* | 2/2010 | Pratt ............... A61M 1/784 700/282 |
| 2010/0042074 A1* | 2/2010 | Weston ............... A61M 1/90 604/543 |
| 2010/0090004 A1 | 4/2010 | Sands et al. |
| 2010/0106528 A1 | 4/2010 | Brackett et al. |
| 2010/0113908 A1 | 5/2010 | Vargas et al. |
| 2010/0145161 A1 | 6/2010 | Niyato et al. |
| 2010/0150991 A1* | 6/2010 | Bernstein ............... A61K 31/00 604/23 |
| 2010/0207768 A1* | 8/2010 | Pidgeon ............... A61M 1/784 340/573.1 |
| 2010/0222645 A1 | 9/2010 | Nadler et al. |
| 2010/0222845 A1* | 9/2010 | Goetz ............... G16H 70/00 607/59 |
| 2010/0234708 A1 | 9/2010 | Buck et al. |
| 2010/0255876 A1 | 10/2010 | Jordan et al. |
| 2011/0004188 A1 | 1/2011 | Shekalim |
| 2011/0063117 A1* | 3/2011 | Turner ............... A61M 1/90 702/50 |
| 2011/0066110 A1 | 3/2011 | Fathallah et al. |
| 2011/0071844 A1 | 3/2011 | Cannon et al. |
| 2011/0073107 A1 | 3/2011 | Rodman et al. |
| 2011/0077605 A1 | 3/2011 | Karpowicz et al. |
| 2011/0092958 A1* | 4/2011 | Jacobs ............... A61M 1/90 604/543 |
| 2011/0106561 A1 | 5/2011 | Eaton, Jr. et al. |
| 2011/0130730 A1* | 6/2011 | Hartwell ............... A61M 1/90 604/319 |
| 2011/0137759 A1 | 6/2011 | Wellington et al. |
| 2011/0145018 A1 | 6/2011 | Fotsch et al. |
| 2011/0173028 A1 | 7/2011 | Bond |
| 2011/0184754 A1 | 7/2011 | Park et al. |
| 2011/0225008 A1 | 9/2011 | Elkouh et al. |
| 2011/0246219 A1 | 10/2011 | Smith et al. |
| 2011/0275353 A1 | 11/2011 | Liu |
| 2011/0288878 A1 | 11/2011 | Blair |
| 2012/0029312 A1 | 2/2012 | Beaudry et al. |
| 2012/0029313 A1 | 2/2012 | Burdett et al. |
| 2012/0032819 A1 | 2/2012 | Chae et al. |
| 2012/0035427 A1 | 2/2012 | Friedman et al. |
| 2012/0035560 A1* | 2/2012 | Eddy ............... A61M 1/74 604/319 |
| 2012/0077605 A1 | 3/2012 | Nakagaito et al. |
| 2012/0081225 A1 | 4/2012 | Waugh et al. |
| 2012/0089369 A1 | 4/2012 | Abuzeni et al. |
| 2012/0123323 A1 | 5/2012 | Kagan et al. |
| 2012/0123796 A1 | 5/2012 | McFaul |
| 2012/0136325 A1* | 5/2012 | Allen ............... A61M 5/48 604/319 |
| 2012/0157889 A1 | 6/2012 | Tanis et al. |
| 2012/0181405 A1 | 7/2012 | Zlatic et al. |
| 2012/0182143 A1 | 7/2012 | Gaines et al. |
| 2012/0185267 A1* | 7/2012 | Kamen ............... A61M 5/1415 705/2 |
| 2012/0191475 A1 | 7/2012 | Pandey |
| 2012/0212455 A1 | 8/2012 | Kloeffel |
| 2012/0215455 A1 | 8/2012 | Patil et al. |
| 2012/0259651 A1 | 10/2012 | Mallon et al. |
| 2012/0271256 A1* | 10/2012 | Locke ............... A61M 1/742 604/319 |
| 2012/0290217 A1 | 11/2012 | Shoval et al. |
| 2012/0295566 A1 | 11/2012 | Collins et al. |
| 2012/0302975 A1* | 11/2012 | Buan ............... A61M 1/73 604/319 |
| 2012/0310205 A1 | 12/2012 | Lee et al. |
| 2013/0018355 A1 | 1/2013 | Brand et al. |
| 2013/0023820 A1* | 1/2013 | Solomon ............... A61M 5/1452 604/66 |
| 2013/0035615 A1 | 2/2013 | Hsieh |
| 2013/0045764 A1 | 2/2013 | Vik et al. |
| 2013/0073303 A1 | 3/2013 | Hsu |
| 2013/0076528 A1 | 3/2013 | Boettner et al. |
| 2013/0087609 A1 | 4/2013 | Nichol et al. |
| 2013/0090949 A1 | 4/2013 | Tibebu |
| 2013/0103419 A1 | 4/2013 | Beaudry |
| 2013/0124227 A1 | 5/2013 | Ellis |
| 2013/0132855 A1 | 5/2013 | Manicka et al. |
| 2013/0150686 A1 | 6/2013 | Fronterhouse et al. |
| 2013/0150698 A1 | 6/2013 | Hsu et al. |
| 2013/0150813 A1* | 6/2013 | Gordon ............... A61M 1/784 604/319 |
| 2013/0151274 A1 | 6/2013 | Bage et al. |
| 2013/0157571 A1 | 6/2013 | Wondka et al. |
| 2013/0159456 A1 | 6/2013 | Daoud et al. |
| 2013/0160082 A1 | 6/2013 | Miller |
| 2013/0186405 A1 | 7/2013 | Krzyzanowski et al. |
| 2013/0190903 A1 | 7/2013 | Balakrishnan et al. |
| 2013/0191513 A1 | 7/2013 | Kamen et al. |
| 2013/0196703 A1 | 8/2013 | Masoud et al. |
| 2013/0204106 A1 | 8/2013 | Bennett |
| 2013/0211206 A1 | 8/2013 | Sands et al. |
| 2013/0211854 A1 | 8/2013 | Wagstaff |
| 2013/0212168 A1 | 8/2013 | Bonasera et al. |
| 2013/0214925 A1 | 8/2013 | Weiss |
| 2013/0218053 A1 | 8/2013 | Kaiser et al. |
| 2013/0226607 A1 | 8/2013 | Woody et al. |
| 2013/0227128 A1 | 8/2013 | Wagstaff |
| 2013/0231596 A1 | 9/2013 | Hornbach et al. |
| 2013/0245387 A1 | 9/2013 | Patel |
| 2013/0253952 A1 | 9/2013 | Burke et al. |
| 2013/0255681 A1 | 10/2013 | Batch et al. |
| 2013/0267919 A1 | 10/2013 | Caso et al. |
| 2013/0268283 A1 | 10/2013 | Vann et al. |
| 2013/0271556 A1 | 10/2013 | Ross et al. |
| 2013/0282395 A1 | 10/2013 | Rustgi et al. |
| 2013/0285837 A1 | 10/2013 | Uchida |
| 2013/0297350 A1 | 11/2013 | Gross et al. |
| 2013/0304489 A1 | 11/2013 | Miller |
| 2013/0310726 A1 | 11/2013 | Miller et al. |

(56) References Cited

U.S. PATENT DOCUMENTS

| | | |
|---|---|---|
| 2013/0317753 A1 | 11/2013 | Kamen et al. |
| 2013/0325508 A1 | 12/2013 | Johnson et al. |
| 2013/0331748 A1 | 12/2013 | Wright et al. |
| 2013/0332197 A1 | 12/2013 | Hinkel |
| 2013/0335233 A1 | 12/2013 | Kamar et al. |
| 2013/0339049 A1 | 12/2013 | Blumberg, Jr. et al. |
| 2013/0345524 A1 | 12/2013 | Meyer et al. |
| 2014/0002234 A1 | 1/2014 | Alwan |
| 2014/0018637 A1 | 1/2014 | Bennett et al. |
| 2014/0028464 A1 | 1/2014 | Garibaldi |
| 2014/0031884 A1 | 1/2014 | Elghazzawi |
| 2014/0032231 A1 | 1/2014 | Semen et al. |
| 2014/0039914 A1* | 2/2014 | Dansereau ............ G16H 50/20 705/2 |
| 2014/0058714 A1 | 2/2014 | Boyer |
| 2014/0087762 A1 | 3/2014 | Galvin et al. |
| 2014/0108033 A1 | 4/2014 | Akbay et al. |
| 2014/0108034 A1 | 4/2014 | Akbay et al. |
| 2014/0108035 A1 | 4/2014 | Akbay et al. |
| 2014/0129250 A1 | 5/2014 | Daniel et al. |
| 2014/0148138 A1 | 5/2014 | Chou |
| 2014/0171753 A1 | 6/2014 | Montejo et al. |
| 2014/0187888 A1 | 7/2014 | Hatziantoniou |
| 2014/0207090 A1 | 7/2014 | Jian |
| 2014/0221788 A1 | 8/2014 | Teller et al. |
| 2014/0222446 A1 | 8/2014 | Ash et al. |
| 2014/0235975 A1 | 8/2014 | Carnes |
| 2014/0244285 A1 | 8/2014 | Hinkle et al. |
| 2014/0244301 A1 | 8/2014 | Lee et al. |
| 2014/0244307 A1 | 8/2014 | Shutko et al. |
| 2014/0266713 A1 | 9/2014 | Sehgal et al. |
| 2014/0275876 A1 | 9/2014 | Hansen et al. |
| 2014/0278502 A1 | 9/2014 | Laskin |
| 2014/0280882 A1 | 9/2014 | Lacerte et al. |
| 2014/0297299 A1 | 10/2014 | Lester, IV |
| 2014/0316819 A1 | 10/2014 | Dunsirn et al. |
| 2014/0350966 A1 | 11/2014 | Khatana et al. |
| 2014/0366878 A1 | 12/2014 | Baron |
| 2014/0371816 A1* | 12/2014 | Matos ................ A61N 1/37247 607/59 |
| 2014/0372147 A1 | 12/2014 | White |
| 2014/0372522 A1 | 12/2014 | Orona et al. |
| 2014/0375470 A1 | 12/2014 | Malveaux |
| 2014/0378895 A1 | 12/2014 | Barack |
| 2015/0012290 A1 | 1/2015 | Inciardi et al. |
| 2015/0019237 A1 | 1/2015 | Doyle et al. |
| 2015/0019257 A1 | 1/2015 | Doyle et al. |
| 2015/0025482 A1* | 1/2015 | Begin .................... A61M 1/90 604/319 |
| 2015/0025486 A1 | 1/2015 | Hu et al. |
| 2015/0046137 A1 | 2/2015 | Zeilinger |
| 2015/0066531 A1 | 3/2015 | Jacobson et al. |
| 2015/0072613 A1 | 3/2015 | Swanson |
| 2015/0094830 A1 | 4/2015 | Lipoma et al. |
| 2015/0095056 A1 | 4/2015 | Ryan et al. |
| 2015/0095059 A1 | 4/2015 | Yegge et al. |
| 2015/0095066 A1 | 4/2015 | Ryan et al. |
| 2015/0100340 A1 | 4/2015 | Folsom et al. |
| 2015/0112707 A1 | 4/2015 | Manice et al. |
| 2015/0118662 A1 | 4/2015 | Ellison et al. |
| 2015/0119652 A1 | 4/2015 | Hyde et al. |
| 2015/0120318 A1 | 4/2015 | Toyama |
| 2015/0133829 A1* | 5/2015 | DeBusk ................ A61M 1/96 601/6 |
| 2015/0143300 A1 | 5/2015 | Zhang et al. |
| 2015/0164323 A1 | 6/2015 | Holtzclaw |
| 2015/0164376 A1 | 6/2015 | Huang |
| 2015/0186615 A1 | 7/2015 | Armor et al. |
| 2015/0189001 A1 | 7/2015 | Lee et al. |
| 2015/0227716 A1 | 8/2015 | Ryan et al. |
| 2015/0227717 A1 | 8/2015 | Ryan et al. |
| 2015/0228043 A1 | 8/2015 | Ryan et al. |
| 2015/0234557 A1 | 8/2015 | Dorn |
| 2015/0234995 A1 | 8/2015 | Casady et al. |
| 2015/0242578 A1 | 8/2015 | Siemon |
| 2015/0242583 A1 | 8/2015 | Edson |
| 2015/0254403 A1 | 9/2015 | Laperna |
| 2015/0257643 A1 | 9/2015 | Watson et al. |
| 2015/0261920 A1 | 9/2015 | Blick |
| 2015/0269323 A1 | 9/2015 | Ginsburg |
| 2015/0286970 A1 | 10/2015 | Dickerson et al. |
| 2015/0304478 A1 | 10/2015 | Kim et al. |
| 2015/0310182 A1 | 10/2015 | Henze et al. |
| 2015/0324943 A1 | 11/2015 | Han et al. |
| 2015/0339445 A1 | 11/2015 | Gruby et al. |
| 2015/0363058 A1 | 12/2015 | Chung et al. |
| 2015/0370984 A1 | 12/2015 | Russell et al. |
| 2015/0370997 A1 | 12/2015 | Krongrad et al. |
| 2015/0379441 A1 | 12/2015 | Syed et al. |
| 2016/0004824 A1 | 1/2016 | Stanton et al. |
| 2016/0018963 A1 | 1/2016 | Robbins et al. |
| 2016/0042154 A1 | 2/2016 | Goldberg et al. |
| 2016/0044141 A1 | 2/2016 | Pfützenreuter et al. |
| 2016/0055310 A1 | 2/2016 | Bentley et al. |
| 2016/0058286 A1 | 3/2016 | Joshua et al. |
| 2016/0063210 A1 | 3/2016 | Bardi et al. |
| 2016/0066864 A1 | 3/2016 | Frieder et al. |
| 2016/0080365 A1 | 3/2016 | Baker et al. |
| 2016/0085415 A1 | 3/2016 | Humphrys et al. |
| 2016/0098524 A1 | 4/2016 | Himmelstein |
| 2016/0110507 A1 | 4/2016 | Abbo |
| 2016/0128571 A1 | 5/2016 | Adler |
| 2016/0129186 A1 | 5/2016 | Douglas et al. |
| 2016/0135752 A1 | 5/2016 | Beaumont |
| 2016/0142443 A1 | 5/2016 | Ting et al. |
| 2016/0151015 A1 | 6/2016 | Condurso et al. |
| 2016/0154936 A1 | 6/2016 | Kalathil |
| 2016/0154943 A1 | 6/2016 | Cho et al. |
| 2016/0171866 A1 | 6/2016 | Dupasquier et al. |
| 2016/0180031 A1 | 6/2016 | Slater |
| 2016/0184497 A1* | 6/2016 | Phillips .................. G16H 40/67 604/319 |
| 2016/0196399 A1 | 7/2016 | Bonhomme |
| 2016/0203275 A1 | 7/2016 | Benjamin et al. |
| 2016/0203283 A1 | 7/2016 | Baruah et al. |
| 2016/0209837 A1 | 7/2016 | Kim |
| 2016/0212577 A1 | 7/2016 | Dor et al. |
| 2016/0217433 A1 | 7/2016 | Walton et al. |
| 2016/0235901 A1* | 8/2016 | Miller ...................... A61M 1/28 |
| 2016/0246943 A1 | 8/2016 | Lake et al. |
| 2016/0260035 A1 | 9/2016 | Crooks et al. |
| 2016/0287189 A1 | 10/2016 | Modai et al. |
| 2016/0308969 A1 | 10/2016 | Aihara et al. |
| 2016/0321404 A1 | 11/2016 | Ginsburg |
| 2016/0321422 A1 | 11/2016 | Albright |
| 2016/0337362 A1* | 11/2016 | Cameron ............ G06Q 20/3278 |
| 2017/0007494 A1 | 1/2017 | Rock et al. |
| 2017/0014028 A1 | 1/2017 | Clear, Jr. |
| 2017/0017765 A1 | 1/2017 | Yegge et al. |
| 2017/0032648 A1 | 2/2017 | McClain et al. |
| 2017/0046503 A1 | 2/2017 | Cho et al. |
| 2017/0053073 A1 | 2/2017 | Allen et al. |
| 2017/0055205 A1 | 2/2017 | Morris et al. |
| 2017/0068781 A1 | 3/2017 | Zasowski et al. |
| 2017/0074717 A1 | 3/2017 | Pilkington et al. |
| 2017/0078396 A1 | 3/2017 | Haas et al. |
| 2017/0116373 A1 | 4/2017 | Ginsburg et al. |
| 2017/0140120 A1 | 5/2017 | Thrower |
| 2017/0150939 A1 | 6/2017 | Shah |
| 2017/0165405 A1* | 6/2017 | Muser ...................... A61M 1/74 |
| 2017/0193181 A1 | 7/2017 | Carter et al. |
| 2017/0212995 A1 | 7/2017 | Ingmanson |
| 2017/0220755 A1 | 8/2017 | Fowler et al. |
| 2017/0257682 A1 | 9/2017 | Shtalryd |
| 2017/0270533 A1 | 9/2017 | Barton et al. |
| 2017/0273116 A1 | 9/2017 | Elghazzawi |
| 2017/0312161 A1 | 11/2017 | Johnson et al. |
| 2017/0327371 A1 | 11/2017 | Bai et al. |
| 2017/0372010 A1 | 12/2017 | Doherty et al. |
| 2018/0004908 A1 | 1/2018 | Barrus et al. |
| 2018/0052454 A1 | 2/2018 | Magno et al. |
| 2018/0121629 A1 | 5/2018 | Dyer et al. |
| 2018/0139572 A1 | 5/2018 | Hansen |
| 2018/0144817 A1 | 5/2018 | Lofgren et al. |

(56) References Cited

U.S. PATENT DOCUMENTS

| | | | |
|---|---|---|---|
| 2018/0158545 A1 | 6/2018 | Blomquist | |
| 2018/0160907 A1 | 6/2018 | Verma | |
| 2018/0181714 A1 | 6/2018 | Pillarisetty et al. | |
| 2018/0224559 A1 | 8/2018 | Park et al. | |
| 2018/0233016 A1 | 8/2018 | Daniel et al. | |
| 2018/0233221 A1 | 8/2018 | Blomquist | |
| 2018/0234499 A1 | 8/2018 | Borges et al. | |
| 2018/0250452 A1* | 9/2018 | Locke | A61M 1/90 |
| 2018/0279880 A1 | 10/2018 | Bacchi | |
| 2018/0280202 A1* | 10/2018 | Pratt | A61M 1/74 |
| 2018/0286502 A1 | 10/2018 | Lane et al. | |
| 2018/0308569 A1 | 10/2018 | Luellen | |
| 2018/0308573 A1 | 10/2018 | Hochrein et al. | |
| 2018/0315492 A1 | 11/2018 | Bishop et al. | |
| 2018/0322944 A1 | 11/2018 | Valdizan | |
| 2019/0151156 A1* | 5/2019 | Kieswetter | A61F 13/00068 |
| 2019/0267127 A1* | 8/2019 | Pemberton | G16H 40/67 |
| 2019/0295718 A1* | 9/2019 | Lawhorn | G16H 20/40 |
| 2019/0307957 A1* | 10/2019 | Worden | A61M 5/142 |
| 2019/0355454 A1* | 11/2019 | Deshpande | G16H 40/67 |
| 2020/0078224 A1* | 3/2020 | Carroll | A61M 1/90 |
| 2021/0030939 A1* | 2/2021 | Heide | G16H 40/67 |
| 2021/0038775 A1* | 2/2021 | Locke | F04B 43/04 |
| 2021/0060217 A1* | 3/2021 | Locke | A61F 13/00068 |
| 2022/0068453 A1* | 3/2022 | Simpson | G16H 10/20 |
| 2022/0257180 A1* | 8/2022 | Armitstead | A61M 16/107 |

FOREIGN PATENT DOCUMENTS

| | | | |
|---|---|---|---|
| DE | 102010036405 A1 | 1/2012 | |
| EP | 0980227 A1 | 2/2000 | |
| EP | 0566381 B1 | 7/2002 | |
| EP | 1231965 A2 | 8/2002 | |
| EP | 1291802 A2 | 3/2003 | |
| EP | 1309960 A1 | 5/2003 | |
| EP | 0814864 B1 | 12/2003 | |
| EP | 1407624 A2 | 4/2004 | |
| EP | 1011420 B1 | 12/2004 | |
| EP | 1495713 A1 | 1/2005 | |
| EP | 1524619 A2 | 4/2005 | |
| EP | 1540557 A2 | 6/2005 | |
| EP | 1579367 A2 | 9/2005 | |
| EP | 1587017 A2 | 10/2005 | |
| EP | 1788503 A2 | 5/2007 | |
| EP | 1839244 A1 | 10/2007 | |
| EP | 1839615 A1 | 10/2007 | |
| EP | 1857950 A2 | 11/2007 | |
| EP | 1870068 A1 | 12/2007 | |
| EP | 1904964 A1 | 4/2008 | |
| EP | 1934852 A1 | 6/2008 | |
| EP | 1975828 A2 | 10/2008 | |
| EP | 1993435 A2 | 11/2008 | |
| EP | 2038786 A2 | 3/2009 | |
| EP | 2040604 A2 | 4/2009 | |
| EP | 2092470 A2 | 8/2009 | |
| EP | 2146297 A1 | 1/2010 | |
| EP | 2172859 A1 | 4/2010 | |
| EP | 2214552 A1 | 8/2010 | |
| EP | 2218478 A1 | 8/2010 | |
| EP | 1404213 B1 | 3/2011 | |
| EP | 1247229 B1 | 4/2011 | |
| EP | 1406540 B1 | 6/2011 | |
| EP | 1812094 B1 | 8/2011 | |
| EP | 2384472 A1 | 11/2011 | |
| EP | 2226002 B1 | 1/2012 | |
| EP | 1610494 B1 | 3/2012 | |
| EP | 1248660 B1 | 4/2012 | |
| EP | 2023800 B1 | 4/2012 | |
| EP | 2451513 A1 | 5/2012 | |
| EP | 1248661 B1 | 8/2012 | |
| EP | 2488977 A1 | 8/2012 | |
| EP | 2562665 A2 | 2/2013 | |
| EP | 2619723 A2 | 7/2013 | |
| EP | 1881784 B1 | 10/2013 | |
| EP | 2664194 A2 | 11/2013 | |
| EP | 2743850 A2 | 6/2014 | |
| EP | 2745204 A1 | 6/2014 | |
| EP | 1684146 B1 | 7/2014 | |
| EP | 2841895 A1 | 3/2015 | |
| EP | 2850771 A1 | 3/2015 | |
| EP | 2876567 A1 | 5/2015 | |
| EP | 2891999 A2 | 7/2015 | |
| EP | 2894581 A1 | 7/2015 | |
| EP | 2906101 A2 | 8/2015 | |
| EP | 2945084 A1 | 11/2015 | |
| EP | 2962266 A1 | 1/2016 | |
| EP | 2968829 A1 | 1/2016 | |
| EP | 2973089 A1 | 1/2016 | |
| EP | 3000082 A1 | 3/2016 | |
| EP | 3010398 A1 | 4/2016 | |
| EP | 3054389 A2 | 8/2016 | |
| EP | 3070628 A1 | 9/2016 | |
| EP | 3078010 A1 | 10/2016 | |
| EP | 3096113 A1 | 11/2016 | |
| EP | 2563437 B1 | 3/2017 | |
| EP | 2773393 B1 | 3/2017 | |
| EP | 3134854 A1 | 3/2017 | |
| EP | 3027242 B1 | 4/2017 | |
| EP | 2556650 B1 | 5/2017 | |
| EP | 3174569 A1 | 6/2017 | |
| EP | 2632407 B1 | 8/2017 | |
| EP | 3209358 A1 | 8/2017 | |
| EP | 3041571 B1 | 9/2017 | |
| EP | 2856767 B1 | 11/2017 | |
| EP | 3252635 A1 | 12/2017 | |
| EP | 2320971 B1 | 5/2018 | |
| EP | 2335173 B1 | 5/2018 | |
| EP | 3100188 B1 | 6/2018 | |
| EP | 3330973 A1 | 6/2018 | |
| EP | 3352174 A1 | 7/2018 | |
| EP | 2440112 B1 | 10/2018 | |
| EP | 3400549 A1 | 11/2018 | |
| EP | 2992500 B1 | 12/2018 | |
| EP | 2597584 B1 | 1/2019 | |
| EP | 3219340 B1 | 1/2019 | |
| EP | 2890456 B1 | 2/2019 | |
| EP | 3377130 B1 | 4/2019 | |
| EP | 2881875 B1 | 5/2019 | |
| EP | 2866851 B1 | 9/2019 | |
| EP | 3899979 A1 | 10/2021 | |
| GB | 2409951 A | 7/2005 | |
| GB | 2436160 A | 9/2007 | |
| GB | 2449400 A | 11/2008 | |
| GB | 2456708 A | 7/2009 | |
| GB | 2423178 B | 5/2010 | |
| GB | 2475091 A | 5/2011 | |
| GB | 2488904 A | 9/2012 | |
| GB | 2446923 B | 5/2013 | |
| GB | 2499986 A | 9/2013 | |
| GB | 2491946 B | 8/2014 | |
| GB | 2499873 B | 5/2016 | |
| GB | 2533910 A | 7/2016 | |
| GB | 2541286 A | 2/2017 | |
| GB | 2550576 B | 6/2018 | |
| WO | WO-9627163 A1 | 9/1996 | |
| WO | WO-9744745 A1 | 11/1997 | |
| WO | WO-9924927 A1 | 5/1999 | |
| WO | WO-9963886 A1 | 12/1999 | |
| WO | WO-0032088 A1 | 6/2000 | |
| WO | WO-0060522 A2 | 10/2000 | |
| WO | WO-0133457 A1 | 5/2001 | |
| WO | WO-0181829 A1 | 11/2001 | |
| WO | WO-0217075 A2 | 2/2002 | |
| WO | WO-0233577 A1 | 4/2002 | |
| WO | WO-02078594 A2 | 10/2002 | |
| WO | WO-02101713 A1 | 12/2002 | |
| WO | WO-03054668 A2 | 7/2003 | |
| WO | WO-2004057514 A2 | 7/2004 | |
| WO | WO-2004074457 A2 | 9/2004 | |
| WO | WO-2005022349 A2 | 3/2005 | |
| WO | WO-2005031632 A2 | 4/2005 | |
| WO | WO-2005036447 A2 | 4/2005 | |
| WO | WO-2005045461 A1 | 5/2005 | |
| WO | WO-2005053793 A1 | 6/2005 | |

(56) References Cited

FOREIGN PATENT DOCUMENTS

| | | |
|---|---|---|
| WO | WO-2005057466 A2 | 6/2005 |
| WO | WO-2005083619 A2 | 9/2005 |
| WO | WO-2005101282 A2 | 10/2005 |
| WO | WO-2005109297 A2 | 11/2005 |
| WO | WO-2005120097 A2 | 12/2005 |
| WO | WO-2006021154 A1 | 3/2006 |
| WO | WO-2006066583 A1 | 6/2006 |
| WO | WO-2006066585 A2 | 6/2006 |
| WO | WO-2006071711 A2 | 7/2006 |
| WO | WO-2006099120 A2 | 9/2006 |
| WO | WO-2006108304 A1 | 10/2006 |
| WO | WO-2006108858 A1 | 10/2006 |
| WO | WO-2006111109 A1 | 10/2006 |
| WO | WO-2007027490 A2 | 3/2007 |
| WO | WO-2007035646 A2 | 3/2007 |
| WO | WO-2007127879 A2 | 11/2007 |
| WO | WO-2007133478 A2 | 11/2007 |
| WO | WO-2007137869 A2 | 12/2007 |
| WO | WO-2008010012 A2 | 1/2008 |
| WO | WO-2008036344 A1 | 3/2008 |
| WO | WO-2008062382 A2 | 5/2008 |
| WO | WO-2008116295 A1 | 10/2008 |
| WO | WO-2008150633 A2 | 12/2008 |
| WO | WO-2009140669 A2 | 11/2009 |
| WO | WO-2010017484 A2 | 2/2010 |
| WO | WO-2010025166 A1 | 3/2010 |
| WO | WO-2010025467 A1 | 3/2010 |
| WO | WO-2010078558 A1 | 7/2010 |
| WO | WO-2010085033 A2 | 7/2010 |
| WO | WO-2010132617 A2 | 11/2010 |
| WO | WO-2010145780 A1 | 12/2010 |
| WO | WO-2011005633 A2 | 1/2011 |
| WO | WO-2011023384 A1 | 3/2011 |
| WO | WO-2011039676 A2 | 4/2011 |
| WO | WO-2011046860 A2 | 4/2011 |
| WO | WO-2011047334 A1 | 4/2011 |
| WO | WO-2011123933 A1 | 10/2011 |
| WO | WO-2011137230 A1 | 11/2011 |
| WO | WO-2012127281 A1 | 9/2012 |
| WO | WO-2013026999 A1 | 2/2013 |
| WO | WO-2013036853 A2 | 3/2013 |
| WO | WO-2013061887 A1 | 5/2013 |
| WO | WO-2013102855 A1 | 7/2013 |
| WO | WO-2013109517 A1 | 7/2013 |
| WO | WO-2013138182 A1 | 9/2013 |
| WO | WO-2013141870 A1 | 9/2013 |
| WO | WO-2013155193 A1 | 10/2013 |
| WO | WO-2013175076 A1 | 11/2013 |
| WO | WO-2014015215 A2 | 1/2014 |
| WO | WO-2014018786 A2 | 1/2014 |
| WO | WO-2014075494 A1 | 5/2014 |
| WO | WO-2014089086 A1 | 6/2014 |
| WO | WO-2014100036 A1 | 6/2014 |
| WO | WO-2014106056 A2 | 7/2014 |
| WO | WO-2014123846 A1 | 8/2014 |
| WO | WO-2014133822 A2 | 9/2014 |
| WO | WO-2014141221 A2 | 9/2014 |
| WO | WO-2014145496 A1 | 9/2014 |
| WO | WO-2014150255 A2 | 9/2014 |
| WO | WO-2014152963 A1 | 9/2014 |
| WO | WO-2014189070 A1 | 11/2014 |
| WO | WO-2014009876 A3 | 12/2014 |
| WO | WO-2015019273 A2 | 2/2015 |
| WO | WO-2015025482 A1 | 2/2015 |
| WO | WO-2015026387 A1 | 2/2015 |
| WO | WO-2015050816 A1 | 4/2015 |
| WO | WO-2015078112 A1 | 6/2015 |
| WO | WO-2015085249 A1 | 6/2015 |
| WO | WO-2015091070 A1 | 6/2015 |
| WO | WO-2015124670 A1 | 8/2015 |
| WO | WO-2015132528 A1 | 9/2015 |
| WO | WO-2015140801 A2 | 9/2015 |
| WO | WO-2015143099 A2 | 9/2015 |
| WO | WO-2015145455 A1 | 10/2015 |
| WO | WO-2015156143 A1 | 10/2015 |
| WO | WO-2015164787 A1 | 10/2015 |
| WO | WO-2015179915 A1 | 12/2015 |
| WO | WO-2015179916 A1 | 12/2015 |
| WO | WO-2015179917 A1 | 12/2015 |
| WO | WO-2015181836 A2 | 12/2015 |
| WO | WO-2015187480 A1 | 12/2015 |
| WO | WO-2016001088 A1 | 1/2016 |
| WO | WO-2016006536 A1 | 1/2016 |
| WO | WO-2016075656 A1 | 5/2016 |
| WO | WO-2016108163 A1 | 7/2016 |
| WO | WO-2016118318 A1 | 7/2016 |
| WO | WO-2016120820 A2 | 8/2016 |
| WO | WO-2016136694 A1 | 9/2016 |
| WO | WO-2016141799 A1 | 9/2016 |
| WO | WO-2016151364 A1 | 9/2016 |
| WO | WO-2016160849 A1 | 10/2016 |
| WO | WO-2016175649 A1 | 11/2016 |
| WO | WO-2016178936 A1 | 11/2016 |
| WO | WO-2016190978 A1 | 12/2016 |
| WO | WO-2017001848 A1 | 1/2017 |
| WO | WO-2017004423 A1 | 1/2017 |
| WO | WO-2017027729 A2 | 2/2017 |
| WO | WO-2017035024 A1 | 3/2017 |
| WO | WO-2017053384 A1 | 3/2017 |
| WO | WO-2017062042 A1 * | 4/2017 .......... A61M 1/0088 |
| WO | WO-2017142100 A1 | 8/2017 |
| WO | WO-2017165895 A1 | 9/2017 |
| WO | WO-2017192673 A1 | 11/2017 |
| WO | WO-2018007100 A1 | 1/2018 |
| WO | WO-2018013666 A1 | 1/2018 |
| WO | WO-2018033819 A1 | 2/2018 |
| WO | WO-2018044894 A1 | 3/2018 |
| WO | WO-2018064234 A1 | 4/2018 |
| WO | WO-2018067593 A2 | 4/2018 |
| WO | WO-2018082813 A1 | 5/2018 |
| WO | WO-2018091492 A1 | 5/2018 |
| WO | WO-2018096390 A1 | 5/2018 |
| WO | WO-2018108724 A1 | 6/2018 |
| WO | WO-2018145880 A1 | 8/2018 |
| WO | WO-2020051273 A1 | 3/2020 |

OTHER PUBLICATIONS

Cinterion., "Cinterion PHS8-P 3G HSPA+," retrieved from http://www.cinterion.com/tl_files/cinterion/downloads/cinterion_datasheet_PHSS_web.pdf, 2012, 2 pages.
International Search Report and Written Opinion for Application No. PCT/EP2019/084611, dated Mar. 17, 2020, 10 pages.
International Preliminary Report on Patentability for Application No. PCT/US2014/026692, dated Sep. 24, 2015, 16 pages.
International Search Report and Written Opinion for Application No. PCT/US2014/026692, dated Mar. 2, 2015, 26 pages.
Invitation to Pay and Partial International Search Report for Application No. PCT/US2014/026692, dated Sep. 26, 2014, 9 pages.

* cited by examiner

SYSTEMS AND METHODS FOR DELIVERING PRESCRIBED WOUND THERAPY

CROSS-REFERENCE TO RELATED APPLICATIONS

This application is a U.S. national stage application of International Patent Application No. PCT/EP2019/084611, filed Dec. 11, 2019, which claims priority to U.K. Provisional Application No. 1820668.0, filed on Dec. 19, 2018; the disclosure of each of which is hereby incorporated by reference in its entirety.

TECHNICAL FIELD

Embodiments of the present disclosure relate to systems, devices, and methods for monitoring and/or treating a wound with, for example with reduced pressure therapy or topical negative pressure (TNP) therapy. In particular, but without limitation, embodiments disclosed herein relate to the delivery of prescribed reduced pressure therapy.

DESCRIPTION OF THE RELATED ART

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds, and abdominal wounds or the like. TNP therapy assists in the closure and healing of wounds by reducing tissue edema, encouraging blood flow, stimulating the formation of granulation tissue, removing excess exudates and may reduce bacterial load. Thus, reducing infection to the wound. Furthermore, TNP therapy permits less outside disturbance of the wound and promotes more rapid healing.

SUMMARY

In some cases, a negative pressure wound therapy device includes a negative pressure source configured to be fluidically connected to a dressing positioned over a wound, the negative pressure source further configured to provide negative pressure therapy to the wound, a user interface configured to receive input from a user and provide feedback to the user, and a controller configured to: receive from the user interface a request to provide negative pressure therapy in accordance with a default therapy prescription, in response to receipt of the request, cause the negative pressure source to provide negative pressure therapy to the wound in accordance with the default therapy prescription, transmit or cause transmission of usage data associated with provision of negative pressure therapy over a time duration to a remote computer and cause the remote computer to monitor compliance with an updated therapy prescription over at least a portion of the time duration, the updated therapy prescription being different than the default therapy prescription, receive an indication from the remote computer that provision of negative therapy over at least the portion of the time duration was non-compliant with the updated therapy prescription, in response to receipt of the indication, provide a non-compliant therapy alert to a user via the user interface and cause receipt from the user interface of an authorization to switch therapy prescription, and in response to receipt of the authorization to switch therapy prescription, cause the negative pressure source to provide negative pressure therapy to the wound in accordance with the updated therapy prescription.

The device of any preceding paragraphs and/or any of the devices disclosed herein can include one or more of the following features. The device can further include a primary power source configured to supply power to at least the negative pressure source and the controller and a secondary power source configured to supply power to at least the user interface and the controller, wherein the controller is configured to provide the non-compliant therapy alert to the user via the user interface when the primary power source is disconnected from the controller or depleted. The secondary power source can be configured to not provide power to the negative pressure source. The controller can be configured to receive the updated therapy prescription from the remote computer and not cause the negative pressure source to provide negative pressure therapy to the wound in accordance with the updated prescription until receipt of the authorization to switch therapy prescription. In response to receipt of the updated therapy prescription, the controller can be further configured to provide an updated therapy prescription alert to the user via the user interface until receipt of the authorization to switch therapy prescription.

The device of any preceding paragraphs and/or any of the devices disclosed herein can include one or more of the following features. Default therapy prescription and updated therapy prescription can specify at least one of therapy duration, therapy intensity, or therapy mode. Usage data can include at least one of therapy duration, therapy intensity, or therapy mode over the time duration. The updated therapy prescription can specify at least one of longer therapy duration, higher therapy intensity, or different therapy mode than the default therapy prescription. The device can include a housing enclosing the negative pressure source and the controller, wherein the user interface is positioned at least partially on an exterior of the housing.

In some cases, a method of operating a negative pressure wound therapy device can include, by at least one processor of the device, receiving, via a user interface of the device, a request to provide negative pressure therapy in accordance with a default therapy prescription, in response to receiving the request, causing a negative pressure source of the device to provide negative pressure therapy in accordance with the default therapy prescription, transmitting or causing transmission of a usage data associated with provision of the negative pressure therapy over a time duration to a remote computer, receiving, from the remote computer, an indication that provision of negative pressure therapy over at least the portion of the time duration was non-compliant with an updated therapy prescription that is different from the default therapy prescription, in response to the receipt of the indication, generating a non-compliance alert via a user interface of the device, obtaining an authorization to switch therapy (such as, the therapy prescription) to the updated therapy prescription, and in response to obtaining the authorization, causing the negative pressure source to provide negative pressure therapy in accordance with the updated therapy prescription.

The method of any preceding paragraphs and/or any of the methods disclosed herein can include one or more of the following features. The default therapy prescription can specify at least one of therapy duration, therapy intensity, or therapy mode. The usage data can include at least one of therapy duration, therapy intensity, or therapy mode over the time duration. The updated therapy prescription can specify at least one of a longer therapy duration, higher therapy intensity, or different therapy mode than the default therapy prescription. The method can include configuring the user interface to enable a user to authorize to switch therapy prescription. The method can include receiving from the remote computer the updated therapy prescription.

In some cases, a system for applying therapy (such as, negative pressure wound therapy) includes a medical device configured to apply or provide treatment according to a default therapy prescription and a remote computing system connected to the medical device via a network, the remote computing system including at least one processor configured to obtain an updated therapy prescription different than the default therapy prescription, receive, from the medical device, usage data associated with provision of the default therapy prescription over a period of time, compare the usage data to an expected usage data associated with the updated therapy prescription, based on the comparison, determine that the usage data is not compliant with the updated therapy prescription, transmit a non-compliance indication to the medical device, receive an authorization to switch (for example, switch treatment) to the updated therapy prescription, and transmit the updated therapy prescription to the medical device.

The system of any preceding paragraphs and/or any of the systems disclosed herein can include one or more of the following features. The default therapy prescription can specify at least one of therapy duration, therapy intensity, or therapy mode. The usage data can include at least one of therapy duration, therapy intensity, or therapy mode over the time duration. The updated therapy prescription can specify at least one of longer therapy duration, higher therapy intensity, or different therapy mode than the default therapy prescription. The at least one processor can be further configured to cause the medical device to apply or provide treatment according to the updated therapy prescription. The medical device can include at least one processor configured to receive an authorization to switch (for example, switch treatment) to the updated therapy prescription from the remote computing device. The medical device can be a negative pressure wound therapy device.

In some cases, a method of operating a medical device includes, by at least one processor, obtaining an updated therapy prescription different than a default therapy prescription according to which treatment is being provided by a medical device. The method can include receiving, from the medical device, usage data associated with provision of the default therapy prescription over a period of time. The method can include comparing the usage data to an expected usage data associated with the updated therapy prescription. The method can include, based on the comparison, determining that the usage data is not compliant with the updated therapy prescription. The method can include transmitting a non-compliance indication to the medical device. The method can include receiving an authorization to switch treatment to the updated therapy prescription. The method can include transmitting the updated therapy prescription to the medical device, thereby causing the medical device to switch treatment to the updated therapy prescription.

The method of any preceding paragraphs and/or any of the methods disclosed herein can include one or more of the following features. Default therapy prescription can specify at least one of therapy duration, therapy intensity, or therapy mode. Usage data can include at least one of therapy duration, therapy intensity, or therapy mode over the time duration. Updated therapy prescription can specify at least one of longer therapy duration, higher therapy intensity, or different therapy mode than the default therapy prescription. Medical device can include a negative pressure wound therapy device.

DETAILED DESCRIPTION

Figure 1:
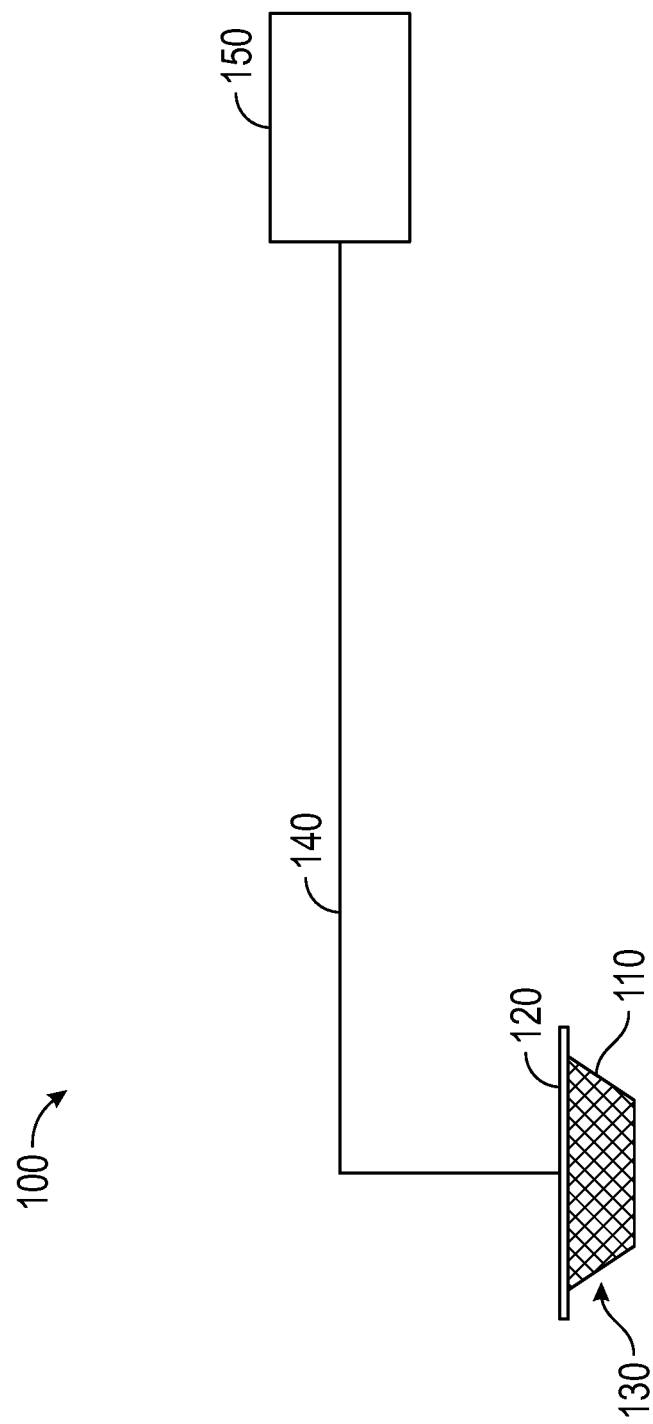
FIG. 1 illustrates a reduced pressure wound therapy system.

Embodiments disclosed herein relate to systems and methods of monitoring and/or treating a wound. It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sternotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Embodiments of systems and methods disclosed herein can be used with topical negative pressure ("TNP") or reduced pressure therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some cases, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects pressure that is X mmHg below 760 mmHg or, in other words, a pressure of (760−X) mmHg. In addition, negative pressure that is "less" or "smaller" than X mmHg corresponds to pressure that is closer to atmospheric pressure (for example, −40 mmHg is less than −60 mmHg). Negative pressure that is "more" or "greater" than −X mmHg corresponds to pressure that is further from atmospheric pressure (for example, −80 mmHg is more than −60 mmHg). In some cases, local ambient atmospheric pressure is used as a reference point, and such local atmospheric pressure may not necessarily be, for example, 760 mmHg.

Systems and methods disclosed herein can be used with other types of treatment in addition to or instead of reduced pressure therapy, such as irrigation, ultrasound, heat and/or cold, neuro stimulation, or the like. In some cases, disclosed systems and methods can be used for wound monitoring without application of additional therapy. Systems and methods disclosed herein can be used in conjunction with a dressing, including with compression dressing, reduced pressure dressing, or the like.

A healthcare provider, such as a clinician, nurse, or the like, can provide a TNP prescription specifying, for example, the pressure level and/or time of application. However, the healing process is different for each patient and the prescription may affect the healing process in a way the clinician or healthcare provider did not expect at the time of devising the prescription. A healthcare provider may try to adjust the prescription as the wound heals (or does not heal), but such process may require various appointments that can be time consuming and repetitive. Embodiments disclosed herein provide systems, devices, and/or methods of efficiently adjusting TNP prescriptions and delivering effective TNP therapy.

Negative Pressure System

FIG. 1 illustrates a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, a negative pressure wound therapy device (sometimes as a whole or partially referred to as a "pump assembly") can be a canisterless (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. In some cases, the wound cover 120 has a top side and a bottom side, and the bottom side adhesively (or in any other suitable manner) seals with wound cavity 110. The conduit 140 or any other conduit disclosed herein can be formed from polyurethane, PVC, nylon, polyethylene, silicone, or any other suitable material.

The wound cover 120 can have a port (not shown) configured to receive an end of the conduit 140. The conduit 140 can otherwise pass through and/or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway or path between the pump assembly 150 and the wound cover 120, so as to supply the reduced pressure provided by the pump assembly 150 to wound cavity 110.

The wound cover 120 and the wound filler 130 can be provided as a single article or an integrated single unit. In some cases, no wound filler is provided and the wound cover by itself may be considered the wound dressing. The wound dressing may then be connected, via the conduit 140, to a source of negative pressure, such as the pump assembly 150. In some cases, though not required, the pump assembly 150 can be miniaturized and portable, although larger conventional pumps such can also be used.

The wound cover 120 can be located over a wound site to be treated. The wound cover 120 can form a substantially sealed cavity or enclosure over the wound site. In some cases, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some cases, the components of the TNP system described herein can be particularly suited for incisional wounds that exude a small amount of wound exudate.

The system can be designed to operate without the use of an exudate canister. The system can be configured to support an exudate canister. In some cases, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

In some cases, the pump assembly 150 can be configured to deliver negative pressure of approximately −80 mmHg, or between about −20 mmHg and −200 mmHg. Note that these pressures are relative to normal ambient atmospheric pressure thus, −200 mmHg would be about 560 mmHg in practical terms. In some cases, the pressure range can be between about −40 mmHg and −150 mmHg. Alternatively, a pressure range of up to −75 mmHg, up to −80 mmHg or over −80 mmHg can be used. Also, in other cases a pressure range of below −75 mmHg can be used. Alternatively, a pressure range of over approximately −100 mmHg, or even 150 mmHg, can be supplied by the pump assembly 150.

In some cases, the pump assembly 150 is configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure set points. Low set point can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High set point can be set at above 25 mmHg, 40 mmHg, 50 mmHg, 60 mmHg, 70 mmHg, 80 mmHg, 90 mmHg, 100 mmHg, 120 mmHg, 140 mmHg, 160 mmHg, 180 mmHg, 200 mmHg, or below −200 mmHg. During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values. The first and second time durations can be selected from the following range: less than 2 minutes, 2 minutes, 3 minutes, 4 minutes, 6 minutes, 8 minutes, 10 minutes, or greater than 10 minutes. In some cases, switching between low and high set points and vice versa can be performed according to a step waveform, square waveform, sinusoidal waveform, and the like.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (such as, wound exudate) is drawn through the conduit 140, and can be stored in a canister. In some cases, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2012/0116334, 2011/0213287, 2011/0282309, 2012/0136325 and U.S. Pat. No. 9,084,845, each of which is incorporated by reference in its entirety. In other embodiments, other suitable wound dressings can be utilized.

Pump Assembly and Canister

Figure 2:
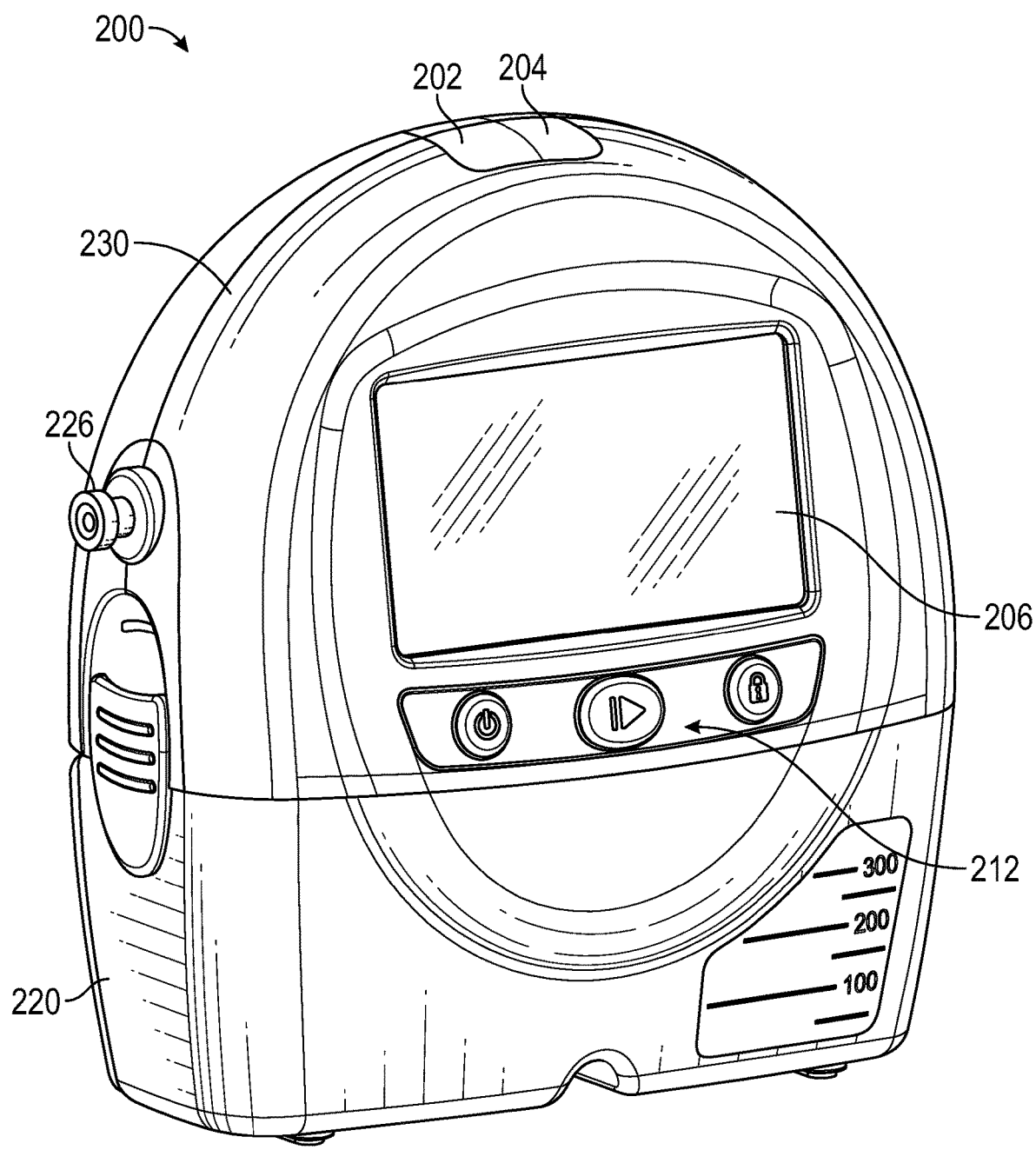
FIG. 2 illustrate a pump assembly and canister.

FIG. 2 illustrates a negative pressure wound therapy device 200 including a pump assembly 230 and canister 220. As is illustrated, the pump assembly 230 and the canister are connected, thereby forming the device 200. The pump assembly 230 comprises one or more indicators, such as visual indicator 202 configured to indicate alarms and visual indicator 204 configured to indicate status of the TNP system. The indicators 202 and 204 can be configured to alert a user to a variety of operating and/or failure conditions of the system, including alerting the user to normal or proper operating conditions, pump failure, power supplied to the pump or power failure, detection of a leak within the wound cover or flow pathway, suction blockage, or any other similar or suitable conditions or combinations thereof. In some cases, any one or more of the indicators 202 and 204 can be configured to alert a user that the current operation is compliant or non-compliant with a therapy prescription, which can be stored in a remote computing device (sometimes referred to a "remote computing system" or "remote computer"). The remote computing device can be any one or more computing devices with at least one processor and/or database, such as one or more cloud servers (sometimes referred to as "the cloud"). In some cases, the pump assembly 230 can comprise additional indicators. In some cases, a single indicator is used. In some cases, multiple indicators are used. Any one or more suitable indicators can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 comprises a display or screen 206 mounted in a recess formed in a case of the pump assembly. In some cases, the display 206 can be a touch screen display. In some cases, the display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion formed in the case of the pump assembly. The gripping portion can be configured to assist the user to hold the pump assembly 230, such as during removal of the canister 220. The pump assembly 230 includes one or more strap mounts 226 for connecting a carry strap to the pump assembly 230 or for attaching a cradle. In some cases, the canister 220 can be replaced with another canister, such as when the canister 220 has been filled with fluid.

The pump assembly 230 comprises one or more keys or buttons 212 configured to allow the user to operate and monitor the operation of the TNP system. As is illustrated, in some cases, there can be a plurality of buttons. One button can be configured as a power button to turn on/off the pump assembly 230. Another button can be configured as a play/pause button for the delivery of negative pressure therapy. For example, pressing the button can cause therapy to start, and pressing the button afterward can cause therapy to pause or end. A button can be configured to lock the display 206 and/or the buttons 212. For instance, a button can be pressed so that the user does not unintentionally alter the delivery of the therapy. In some cases, multiple key presses and/or sequences of key presses can be used to operate the pump assembly 230.

The canister 220 is configured to hold fluid (such as, exudate) removed from the wound cavity 110. The canister 220 includes one or more latches for attaching the canister to the pump assembly 230. The exterior of the canister 220 can be formed from frosted plastic so that the canister is substantially opaque and the contents of the canister and substantially hidden from plain view. The canister 220 includes a substantially transparent window, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. The canister 220 comprises a tubing channel for connecting to the conduit 140.

In some cases, the pump assembly 230 comprises a power jack for charging and recharging a primary power source, such as an internal battery, of the pump assembly. In some cases, the power jack is a direct current (DC) jack. In some cases, the pump assembly can comprise a disposable primary power source, such as batteries, so that no power jack is needed. In some cases, the pump assembly 230 comprises two or more power sources or supplies. In some cases, one of the power supplies (for example, primary) can deliver power to operate and control the pump. In some cases, a secondary power source can deliver power to one or more of the user interface, alert system, and/or communication system for uploading usage data to the cloud.

Control System

Figure 3:
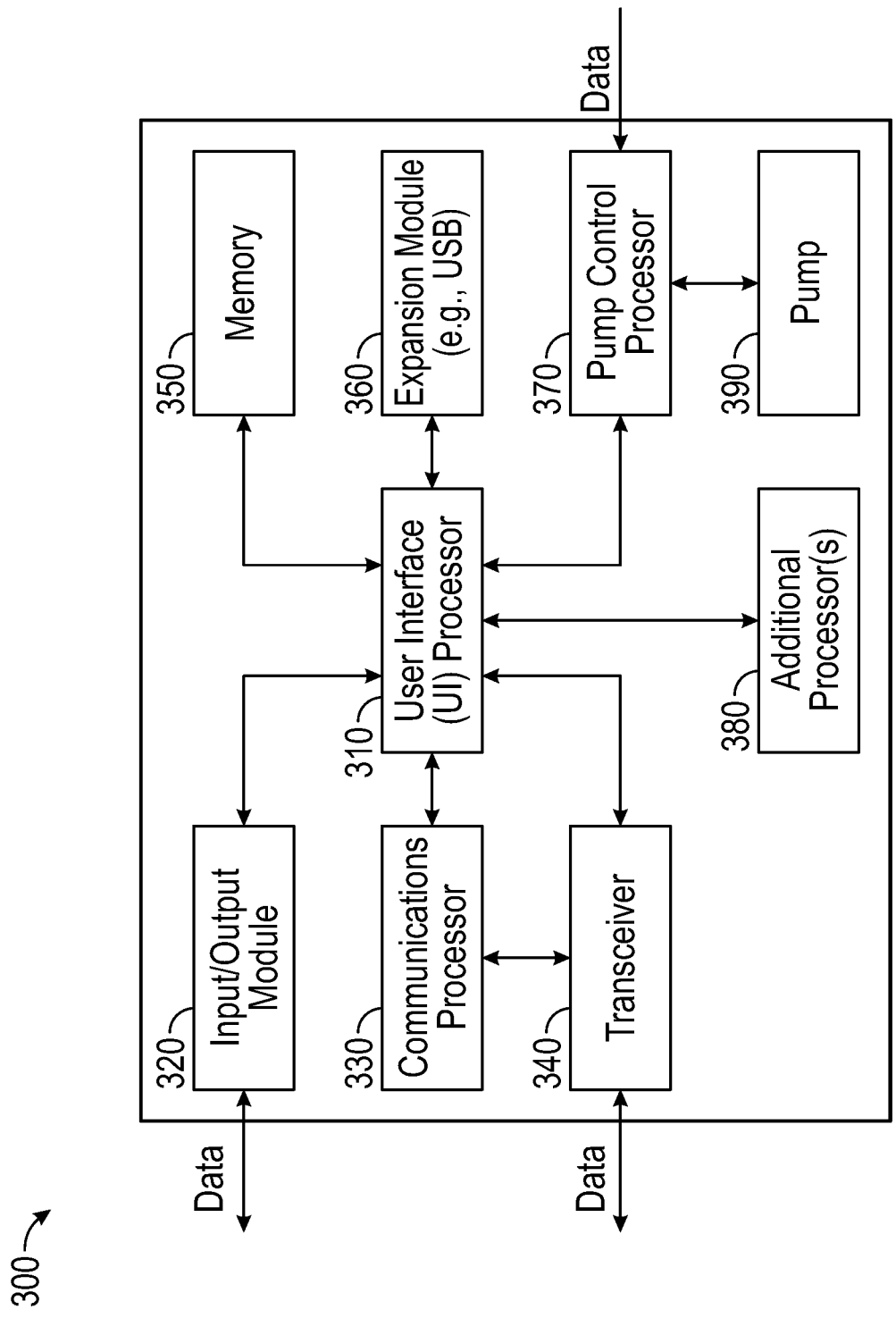
FIG. 3 illustrates a schematic of a reduced pressure wound therapy system.

FIG. 3 illustrates a schematic of a control system 300 which can be employed in any of the embodiments of wound monitoring and/or treatment systems described herein. Electrical components can operate to accept user input, provide output to the user, operate the negative pressure source of a TNP system, provide network connectivity, and so on. It may be advantageous to utilize multiple processors in order to allocate or assign various tasks to different processors. In some cases, a first processor can be responsible for user activity and a second processor can be responsible for controlling another device, such as a pump 390. This way, the activity of controlling the other device, such as the pump 390, which may necessitate a higher level of responsiveness (corresponding to higher risk level), can be offloaded to a dedicated processor and, thereby, will not be interrupted by user interface tasks, which may take longer to complete because of interactions with the user.

Input and output to the other device, such as a pump 390, one or more sensors (for example, one or more pressure sensors configured to monitor pressure in one or more locations of the fluid flow path), or the like, can be controlled by an input/output (I/O) module 320. For example, the I/O module can receive data from one or more sensors through one or more ports, such as serial (for example, I2C), parallel, hybrid ports, and the like. The processor 310 also receives data from and provides data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, stores data in one or more memory modules 350, which can be internal and/or external to the processor 310. Any suitable type of memory can be used, including volatile and/or non-volatile memory, such as RAM, ROM, magnetic memory, solid-state memory, Magnetoresistive random-access memory (MRAM), and the like.

In some cases, the processor 310 can be a general purpose controller, such as a low-power processor. In other cases, the processor 310 can be an application specific processor. In some cases, the processor 310 can be configured as a "central" processor in the electronic architecture of the system 300, and the processor 310 can coordinate the activity of other processors, such as a pump control processor 370, communications processor 330, and one or more additional processors 380. The processor 310 can run a suitable operating system, such as a Linux, Windows CE, VxWorks, etc.

The pump control processor 370 (if present) can be configured to control the operation of a negative pressure pump 390. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. In some cases, the pump control processor 370 can measure pressure in a fluid flow path, using data received from one or more pressure sensors, calculate the rate of fluid flow, and control the pump. In some cases, the pump control processor 370 controls the pump motor so that a desired level of negative pressure in achieved in the wound cavity 110. The desired level of negative pressure can be pressure set or selected by the user. The pump control processor 370 can control the pump (for example, pump motor) using pulse-width modulation (PWM). A control signal for driving the pump can be a 0-100% duty cycle PWM signal. The pump control processor 370 can perform flow rate calculations and detect alarms. The pump control processor 370 can communicate information to the processor 310. The pump control processor 370 can include internal memory and/or can utilize memory 350. The pump control processor 370 can be a low-power processor.

A communications processor 330 can be configured to provide wired and/or wireless connectivity. The communications processor 330 can utilize one or more antennas or transceivers 340 for sending and receiving data. In some cases, the communications processor 330 can provide one or more of the following types of connections: Global Positioning System (GPS) technology, cellular connectivity (for example, 2G, 3G, LTE, 4G, 5G, or the like), WiFi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software and/or firmware, and the like. In some cases, the communications processor 330 can provide dual GPS/cellular functionality. Cellular functionality can, for example, be 3G functionality. In such cases, if the GPS module is not be able to establish satellite connection due to various factors including atmospheric conditions, building or terrain interference, satellite geometry, and so on, the device location can be determined using the 3G network connection, such as by using cell identification, triangulation, forward link timing, and the like. In some cases, the system 300 can include a SIM card, and SIM-based positional information can be obtained. The communications processor 330 can communicate information to the processor 310. The communications processor 330 can include internal memory and/or can utilize memory 350. The communications processor 330 can be a low-power processor.

In some cases, the system 300 can store data illustrated in Table 1. This data can be stored, for example, in memory 350. This data can include patient data collected by one or more sensors. In various cases, different or additional data can be stored by system 300. In some cases, location information can be acquired by GPS or any other suitable method, such as cellular triangulation, cell identification forward link timing, and the like.

TABLE 1

| Example Data Stored | | | |
| --- | --- | --- | --- |
| Category | Item | Type | Source |
| GPS | Location | Latitude, Longitude, Altitude | Acquired from GPS |
|  | Timestamp Location Acquired | Timestamp |  |
| Therapy | Total time therapy ON since device activation | Minutes | Calculated on device based on user control |
|  | Total time therapy ON since last maintenance reset | Minutes |  |
|  | Device Placement; | Minutes |  |

TABLE 1-continued

Example Data Stored

| Category | Item | Type | Source |
|---|---|---|---|
| | accumulated daily hours starting from first Therapy ON after last maintenance reset, stopping at last Therapy OFF before returning for Maintenance and maintenance reset. (Includes both THERAPY ON and THERAPY OFF hours) | | |
| Device | Serial Number | Alphanumeric | Set by Pump Utility |
| | Controller Firmware Version | Alphanumeric | Unique version identifier, hard coded in firmware |
| Events | Device Event Log (See Table 3 for example) | List of Events (See Table 2) | Generated in response to various user actions and detected events |

The system 300 can track and log therapy and other operational data. Such data can be stored, for example, in the memory 350. In some cases, the system 300 can store log data illustrated in Table 2. Table 3 illustrates an example event log. One or more such event logs can be stored by the system 300. As is illustrated, the event log can include time stamps indicating the time of occurrence. In some cases, additional and/or alternative data can be logged.

TABLE 2

Example Data Tracked

| Category | ID | Type | Data Content | Notes |
|---|---|---|---|---|
| Device | 0 | Startup (Created DB) | | First time, out-of-the-box. |
| | 1 | Startup (Resumed DB) | | Subsequent power-ups. |
| | 2 | Startup (Corrupt DB, Recreated) | | Corrupt configuration was detected. The database was deleted and recreated, and next run was in out-of-the-box mode. |
| | 3 | Shutdown (Signaled) | | Normal shutdown, handled/registered by software. |
| | 4 | Shutdown (Inferred) | | Unexpected shutdown: on next power-up, last active time registered as shutdown event. |
| Therapy | 5 | Start Delivery (Continuous) | modes, setpoints | Modes are Y-connect status, and intensity. |
| | 6 | Start Delivery (Intermittent) | modes, setpoints | Modes are Y-connect status, and intensity. |
| | 7 | Stop Delivery | | |
| | 8 | Set Therapy Pressure Setpoint | mmHg | This and other therapy adjustment events are only recorded while therapy is being delivered. |
| | 9 | Set Standby Pressure Setpoint | mmHg | |
| | 10 | Set Intermittent Therapy Duration | setting (30 s, 60 s, etc) | |
| | 11 | Set Intermittent Standby Duration | setting (30 s, 60 s, etc) | |
| | 12 | SetMode | cont/intermittent | |
| | 13 | Set Intensity | low/med/high | |
| | 14 | Set Y Connect | yes/no | |
| Alarm | 15 | Over Vacuum | high mmHg | |
| | 16 | High Vacuum | high deviation mmHg | |
| | 17 | Blocked Full Canister | low airflow lpm | |
| | 18 | High Flow Leak | high airflow lpm | |
| | 19 | Low Vacuum | low mmHg | |
| | 20 | Battery Failure | | |
| | 21 | Critical Battery | | |
| | 22 | Low Battery | | |
| | 23 | Inactivity | | |
| Maintenance | 24 | Maintenance Reset | | |
| | 25 | Reset to Defaults | | |
| | 26 | Software/Device Warning | Warning code | Any detected, minor unexpected software behavior will be logged as an event |
| | 27 | Software/Device Fault | Fault code | Any detected, severe unexpected software behavior will be logged as an event |

TABLE 3

Example Event Log

| Timestamp | Type ID | Type Description | Data |
|---|---|---|---|
| 1:23:45 Apr. 2, 2012 (UTC-12) | 0 | Startup (Created DB) | |
| 1:29:23 Apr. 2, 2012 (UTC-12) | 15 | Set Intensity | medium |
| 1:29:43 Apr. 2, 2012 (UTC-12) | 10 | Set Therapy Pressure Setpoint | 120 mmHg |
| 1:31:02 Apr. 2, 2012 (UTC 12) | 7 | Start Delivery (Continuous) | 120 mmHg continuous, medium intensity, no Y connect |
| 1:44:20 Apr. 2, 2012 (UTC-12) | 20 | High Flow Leak | 4 lpm |
| 1:44:24 Apr. 2, 2012 (UTC-12) | 9 | Stop Delivery | |

In some cases, using the connectivity provided by the communications processor 330, the system 300 can upload any of the data stored, maintained, and/or tracked by the system 300 to a remote computing device. In some cases, the following information can be uploaded to the remote computing device: activity log(s), which includes therapy delivery information, such as therapy duration, alarm log(s), which includes alarm type and time of occurrence; error log, which includes internal error information, transmission errors, and the like; therapy duration information, which can be computed hourly, daily, and the like; total therapy time, which includes therapy duration from first applying a particular therapy program or programs; lifetime therapy information; device information, such as the serial number, software version, battery level, etc.; device location information; patient information; and so on. The system 300 can also download various operational data, such as therapy selection and parameters, firmware and software patches and upgrades, and the like. The system 300 can provide Internet browsing functionality using one or more browser programs, mail programs, application software (for example, apps), etc. Additional processors 380, such as processor for controlling one or more user interfaces (such as, one or more displays), can be utilized. In some cases, any of the illustrated and/or described components of the system 300 can be omitted depending on an embodiment of a wound monitoring and/or treatment system in which the system 300 is used.

Figure 4:
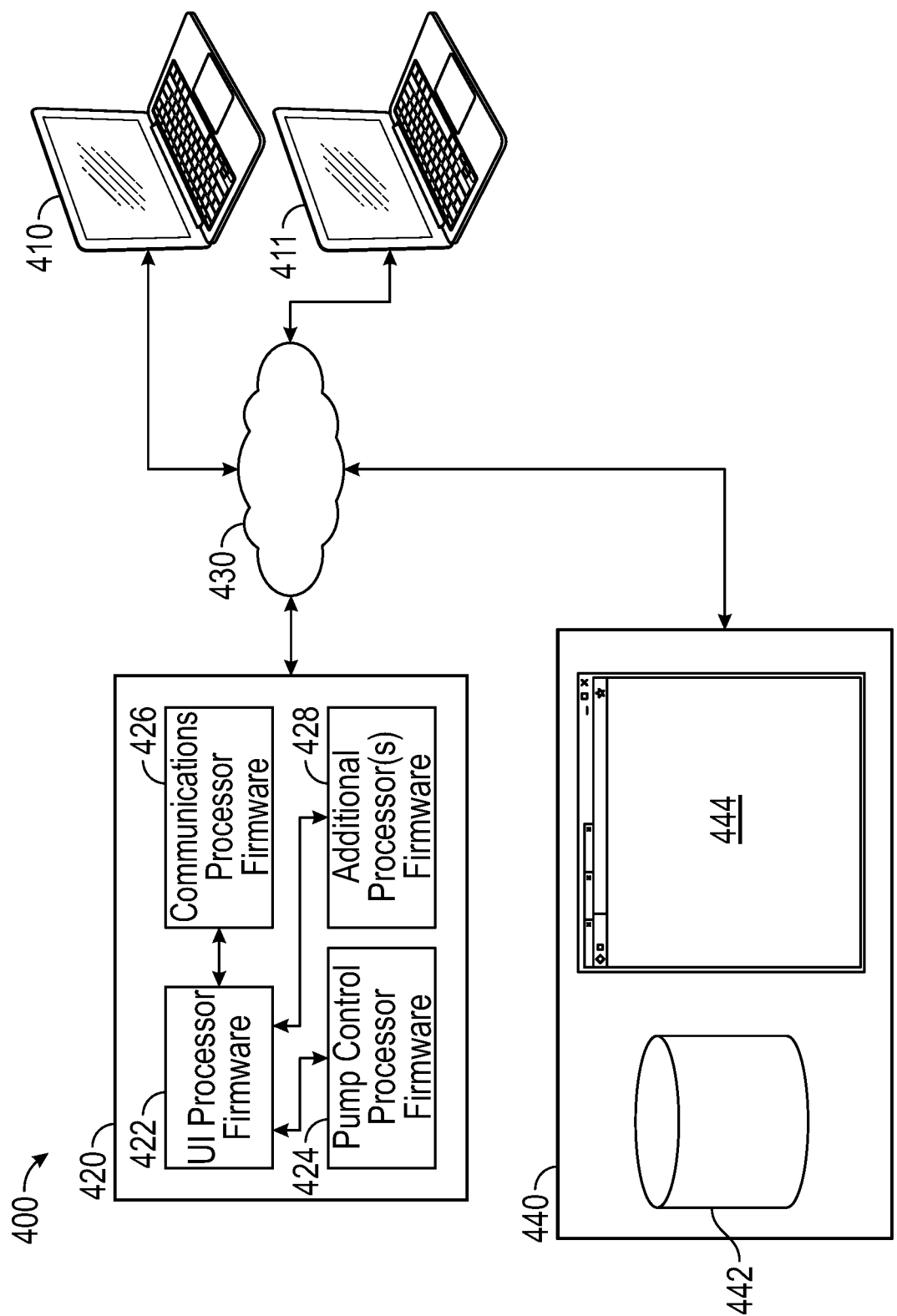
FIG. 4 illustrates a schematic of a reduced pressure wound therapy system connected over a network.

FIG. 4 illustrates a schematic of a reduced pressure wound therapy system 400. A pump assembly 420 includes a user interface processor firmware and/or software 422, which can be executed by the user interface processor 310, pump control processor firmware and/or software, which can be executed by the pump control processor 370, communications processor firmware and/or software 426, which can be executed by the communications processor 330, and additional processor(s) firmware and/or software, which can be executed by one or more additional processors 380. The pump assembly 420 can be connected to one or more remote computing device 410, 411, 440 via a network 430. In some cases, the pump assembly 420 can be directly connected to one or more devices 410, 411, 440, which can be a laptop, desktop, tablet, smartphone, server, and the like. A wired or wireless connection can be utilized to connect the one or more devices 410, 411, 440 to the pump assembly 420. The connection between the one or more devices 410, 411, 440 and the pump assembly 420 can be used for various activities, such as pump assembly location tracking, asset tracking, compliance monitoring, selection, uploading of logs, alarms, and other operational data, and adjustment of therapy settings, upgrading of software and/or firmware, and the like. The pump assembly 420 and one or more devices 410, 411 can communicate with device 440, which can be a server, via the network 430. The server 440 can include a data storage module 442 and a web interface 444 for accessing the server.

The connection between the one or more devices 410, 411, 440 and the pump assembly 420 can be utilized to perform one or more of the following: initialization and programming of the pump assembly 420, firmware and/or software upgrades, maintenance and troubleshooting, selecting and adjusting therapy parameters, and the like. In some cases, the one or more devices 410, 411, 440 can execute an application program for communicating with the pump assembly 420.

The pump assembly 420 can upload various data to the server 440 via the network 430. In some cases, the pump assembly 420 can upload data to one or more remote computing devices, such as one or more servers. As explained above, upload data can include activity log(s), alarm log(s), usage data, therapy duration information, total therapy time, lifetime therapy information, device information, device location information, patient information, etc. In addition, the pump assembly 420 can receive and process commands received from the network 430

Further description of a negative pressure wound therapy system and its operation that may be used with any of the embodiments of the present application is found in U.S. Pat. No. 9,737,649, which is incorporated by reference in its entirety.

Adjusting the Therapy Prescription

In some cases, a reduced pressure device can be configured to collect information from the patient, such as:

How painful is the wound (scale 1-10)
Has the exudate colour changed?
Is there any smell?
Is there anything wrong?

The data can be collected periodically, for example, daily, several times a day, every other day, or the like. The data can be collected via the user interface. For example, the data can be collected via a daily pop up screen. The data could alternatively or additionally be inputted via a stand-alone application on a computing device, such as a smart phone, tablet, laptop computer, or the like. The data can be transmitted to a remote computing system, which can make the data available to a healthcare provider. The healthcare provider may use the information to prescribe a new or updated therapy prescription. For example, if there is pain, negative pressure may be reduced. As another example, if there is odour, infection may be present.

In some cases, the therapy prescription can be updated as the healing progresses. For example, a healthcare provider can apply a default prescription when prescribing the device but update the prescription with more complex adjustments as he or she assesses the healing of the wound. When a reduced pressure therapy device is prescribed to a patient, a default therapy prescription can be set. A default therapy prescription can be automatically loaded onto the reduced pressure therapy device. The default prescription may be the only therapy accessible on the device for the particular healthcare provider without inserting or entering an access code. The default therapy prescription may be factory set or set by a senior clinical administrator. The default therapy prescription may only be a basic safe operating therapy. For example, the default therapy prescription may not include therapy duration, and the healthcare provider may be required to set the duration on the device or remotely. Capability to apply the default therapy prescription may allow a junior clinician or nurse to apply the device and start a safe protocol therapy without delay in determining more tailored therapy parameters.

A healthcare provider, such as the clinician or nurse, can select the default therapy prescription via a user interface. After the default therapy is prescribed, the reduced pressure therapy device transmits compliance or usage data to a remote computer. The reduced pressure therapy device can record and/or transmit usage data to a remote computer for a period of time, such as 1 hour, 3 hours, half a day, 1 day, or the like. In some cases, the period of time can be defined via the reduced pressure therapy device. In some cases, the period of time can be defined via the remote computing device.

Usage data can be indicative of how the device is being used for delivering therapy. For example, usage data can include one or more of the number of treatments that have been performed, the date and time that each treatment is performed, duration of each treatment, and/or the like. As another example, usage data can comprise amount of time the device was turned on, applied therapy over time, amount of aspirated exudate, and/or the like. As yet another example, usage data can comprise biometric information, such as tissue impedance, temperature, wound image information, and/or the like.

The remote computing device can receive usage data from the reduced pressure therapy device and monitor the usage data to generate compliance information. Compliance information can be indicative of the usage of the device complying with a therapy prescription, such as the current therapy prescription. The usage data can indicate the manner in which treatments were performed using the device, from which a patient's compliance with a particular treatment prescription can be determined.

In some cases, a patient's compliance with prescribed therapy is determined with respect to an updated therapy prescription. A user, such as a senior clinician or doctor, can enter updated therapy prescription information via the remote computing device. The user can determine an updated therapy prescription based on the received usage data from the reduced pressure therapy device. The updated therapy prescription can include a different applied pressure setting and/or durational setting. The updated therapy prescription can specify a different therapy intensity or therapy mode. Some embodiments disclosed herein allow the user to propose an updated therapy prescription after the patient has received at least some therapy and after at least some information regarding the healing progress is available.

Further description of determining compliance that may be used with any of the embodiments of the present application is found in U.S. Pat. No. 9,526,920, which is incorporated by reference in its entirety.

In some cases, if the remote computing device detects that the received usage data is non-compliant with the updated therapy prescription, the remote computing device can generate an indication or alert indicative of non-compliance. The alert can be transmitted to the reduced pressure therapy device. The alert can be displayed on the user interface of the reduced pressure therapy device. In some cases, before switching therapy to the updated prescription, the updated prescription should first be verified by a healthcare provider. This can be performed manually at the reduced pressure therapy device (such as, via the user interface) or remotely. For example, upon receipt of the alert, the user interface of the reduced pressure therapy device can prompt the user, such as a clinician, nurse, or user, to authorize a switch to the updated therapy prescription. Authorization can be performed manually, such as at the user Interface of the device, or remotely, such as via the remote computing device. In response to the authorization and/or as part of transmitting the non-compliance alert, the remote computing system can transmit the updated therapy prescription to the reduced pressure therapy device, which then can apply the updated therapy prescription once authorization has been received. The remote computing system can transmit the updated therapy prescription before the reduced pressure therapy device has received authorization for the prescription switch. In some cases, the updated therapy prescription is stored on the reduced pressure therapy device but is applied when the user inputs authorization.

In some cases, an indication or alert that an updated prescription has been sent to the reduced pressure therapy device can be transmitted from the remote computing device and/or generated by the reduced pressure therapy device. This updated therapy prescription alert can be separate from the non-compliance alert. This alert can be provided to the user as described herein, such as via the user interface, to facilitate authorization of the updated prescription.

Further description of authorization that may be used with any of the embodiments of the present application is found in International Patent Application No. PCT/EP2019/081248, which is incorporated by reference in its entirety.

In some cases, a default therapy prescription may be applied to override the factory default. This can be applied by a local clinician or engineer. In some cases, the prescription may be stored in the remote computing device and may be assigned to one or a number of devices registered with the remote computing device. Each device may have a unique identification code that may be stored in the device and the remote computing device, making it possible to account for each device.

In some instances, a tailored therapy prescription may already be set by and/or on the remote computing device. On power up (or at another time), the reduced pressure wound therapy device may check the remote computing device for the most current therapy setting and provide an alert that a new prescription is awaiting acceptance as described herein.

In some cases, the alerts for non-compliance and/or updated therapy prescription can be received by the reduced pressure therapy system and/or provided to the user even when the pump assembly is powered off and/or when a primary power source is depleted. When the pump assembly is turned off, the primary power source can be disconnected from at least some of the electric components, such as from the negative pressure source. The primary power source could be depleted so that it cannot supply sufficient power to operate the at least some of the electric components, such as the negative pressure source and/or one or more processors. The secondary power source can serve as a back-up power source that provides sufficient power to allow provision of at least one of the non-compliant therapy or the updated therapy prescription alert when the primary power source is disconnected and/or depleted. In some cases, the user interface can be powered by a secondary power source. In some cases, usage data is transmitted even when the pump assembly is powered off and/or the primary power source is depleted. In such cases, the communication system can be powered by a secondary power source. The secondary power source can include one or more supercapacitors.

At least some embodiments disclosed herein advantageously allow for therapy to be applied quicker and more effectively than with traditional systems. A healthcare provider can setup the reduced pressure therapy device to apply therapy to the patient according to a default therapy prescription, as described herein, without having to determine optimal therapy prescription and/or receive extensive training on how to operate the device. Such default therapy prescription can be pre-loaded on the device, making it easier to cause provision of therapy to the patient according to the default therapy prescription. While the patient receives therapy according to the default therapy prescription, the same healthcare provider (or a more experienced or knowledgeable healthcare provider, such as a senior clinician) can update the therapy prescription to be more tailored to the patient's needs. This can be performed remotely based on the data received from the device, as described herein. Non-compliance with the updated therapy prescription can be determined as described herein, which can cause generation and display of the alert, leading to a switch in the therapy prescription and application of therapy to the patient according to the updated therapy prescription. Accordingly, therapy time and effectiveness can be maximized.

For example, a reduced pressure therapy device can be first applied by a healthcare provider to a patient according to instructions for use and local medical protocols. The device may on power up be configured to access a default safe and efficacious therapy prescription settings (for instance, from non-volatile memory), and on selection of start therapy, the default therapy prescription to the patient.

The default therapy settings may include a compliant therapy use threshold, such as to exceed 22 hours of use in any 24 hours. Initialization of therapy may allow for any troubleshooting to occur. The application of therapy may cause the default therapy setting to be sent to a remote computing device along with an indication of a new application of therapy and/or any other information, such as location, clinician name, patient ID, and/or the like. Once the data message is received, alerts may be sent to administrators and/or healthcare providers via any transmission means, such as email, SMS, etc. indicating a new application of therapy according to the default therapy prescription has occurred. A response to confirm acceptance or to change the settings may be required. Acceptance (for example, via SMS message, reply email, or via log-on to the remote computing device through an application) can confirm monitoring against the default therapy setting identified in the acceptance message. Alternatively, the therapy prescription may be changed according to the individual requirements of the patient. Changing the prescription results in the prescription being sent to the device and logged in the remote computing system. On receipt of the new prescription at the device, an alert can be indicated on the device that a new prescription is waiting to be accepted. Acceptance of the prescription may only be carried out by input of an authorization password or a biometric check (for example, a finger print check being completed by the clinician at the device and acceptance of the new settings displayed).

The device may send telemetry/status data updates to the remote computing device periodically and/or in real time. The remote computing device can generate alerts for non-compliant application of the prescription stored in the remote computing device. For example, usage time may be below the threshold, application of pressure(s) may be outside a threshold range, and/or any suitable deviation from the prescription that may mean therapy is not being delivered at a therapeutic level. Non-compliance alerts may be sent remotely to the device and/or to the healthcare providers registered with the remote computing device via any of the messaging techniques described herein.

Figure 5:
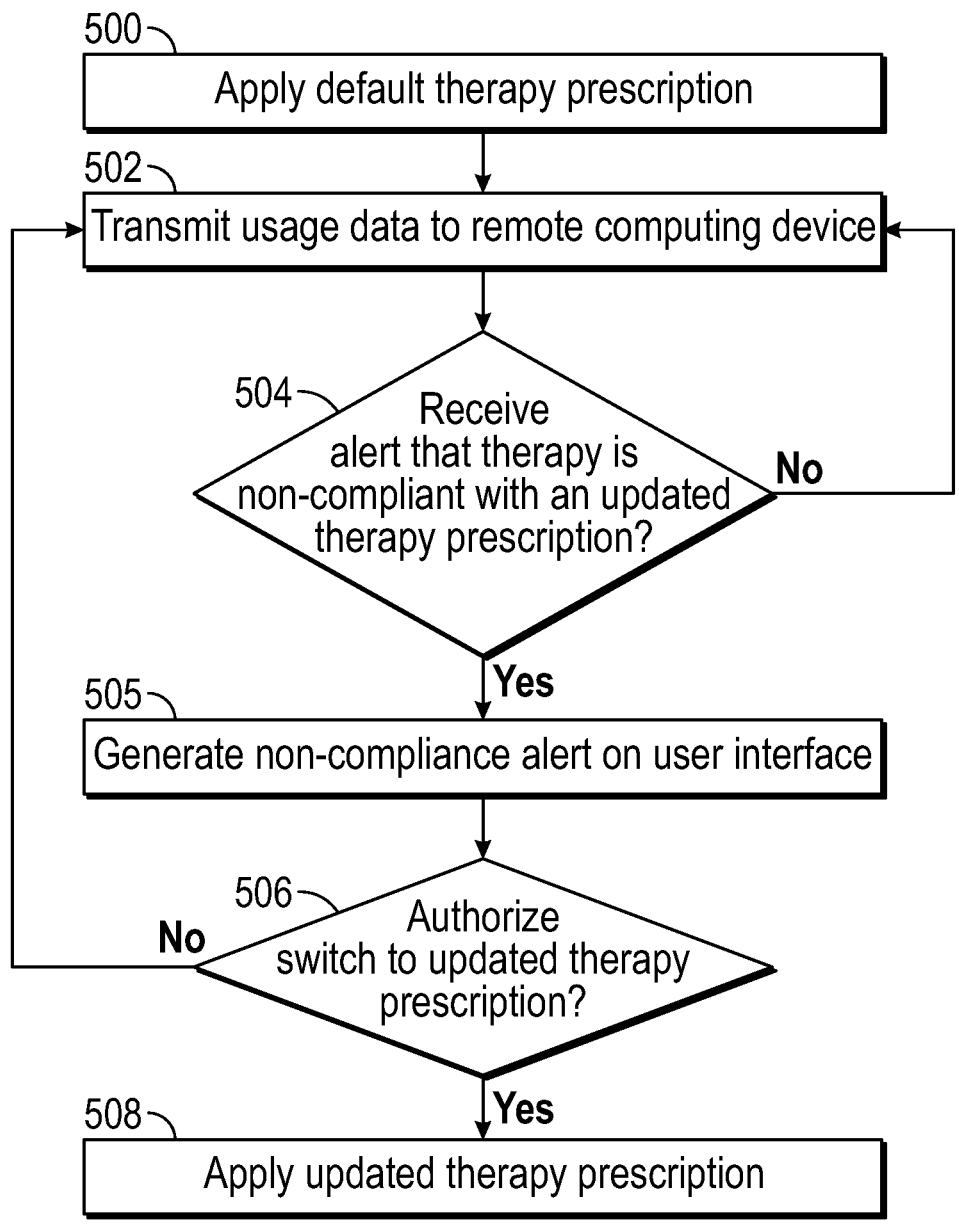
FIG. 5 illustrates a process of operating a negative pressure wound therapy system.

FIG. 5 illustrates a process of operating a reduced pressure wound therapy device. The illustrated process can be implemented by any of the reduced pressure wound therapy devices disclosed herein, and in particular by at least one processor of the reduced pressure wound therapy device. The process can start in block 500 when the reduced pressure therapy device provides therapy to a wound of a patient according to a default therapy prescription. In some cases, the default therapy prescription specifies a minimum pressure applied to the wound. In some cases, the default therapy prescription specifies time intervals in which the minimum pressure is applied. In some cases, the default therapy prescription specifies control rules that adjust the applied pressure. In block 502, the process can transmit usage data to a remote computing device. Such transmission can be performed periodically as described herein. The usage data can comprise applied pressure over time, amount of exudate aspirated from the wound, the amount of time the therapy has been applied, and/or the like. In some cases, the usage data additionally or alternatively comprises biometric information as described herein. At block 504, the process determines whether the device has received an alert that the currently administered therapy is non-compliant. The process can receive the updated therapy prescription as described herein, such as in block 504. In some cases, block 504 is executed periodically at time intervals. In some cases, block 504 is executed continuously.

If the process does not receive the non-compliance alert and/or the updated therapy prescription, the process can return to block 502 and continue to monitor and/or transmit usage data to the remote computing device. If the process receives the alert and/or the updated therapy prescription, the process can proceed to block 505. In block 505, the process can communicate one or more of the non-compliant or updated therapy prescription alerts to the user via the user interface. In block 506, the process can determine whether to authorize a switch to the updated therapy prescription as set at or by the remote computing device. In some cases, the decision to or not to authorize the update can be made via the user interface, such as via one or more buttons, a touch screen, fingerprint reader, or the like. In some cases, the decision to authorize can be made on the remote computing device. If the update is not authorized, the process can return to block 502 and continue to transmit usage data to the remote computing device. The process can continue to provide one or more of the non-compliance or updated prescription alerts to the user. If the update is authorized, the process can cause application of therapy according to the updated therapy prescription in block 508.

Figure 6:
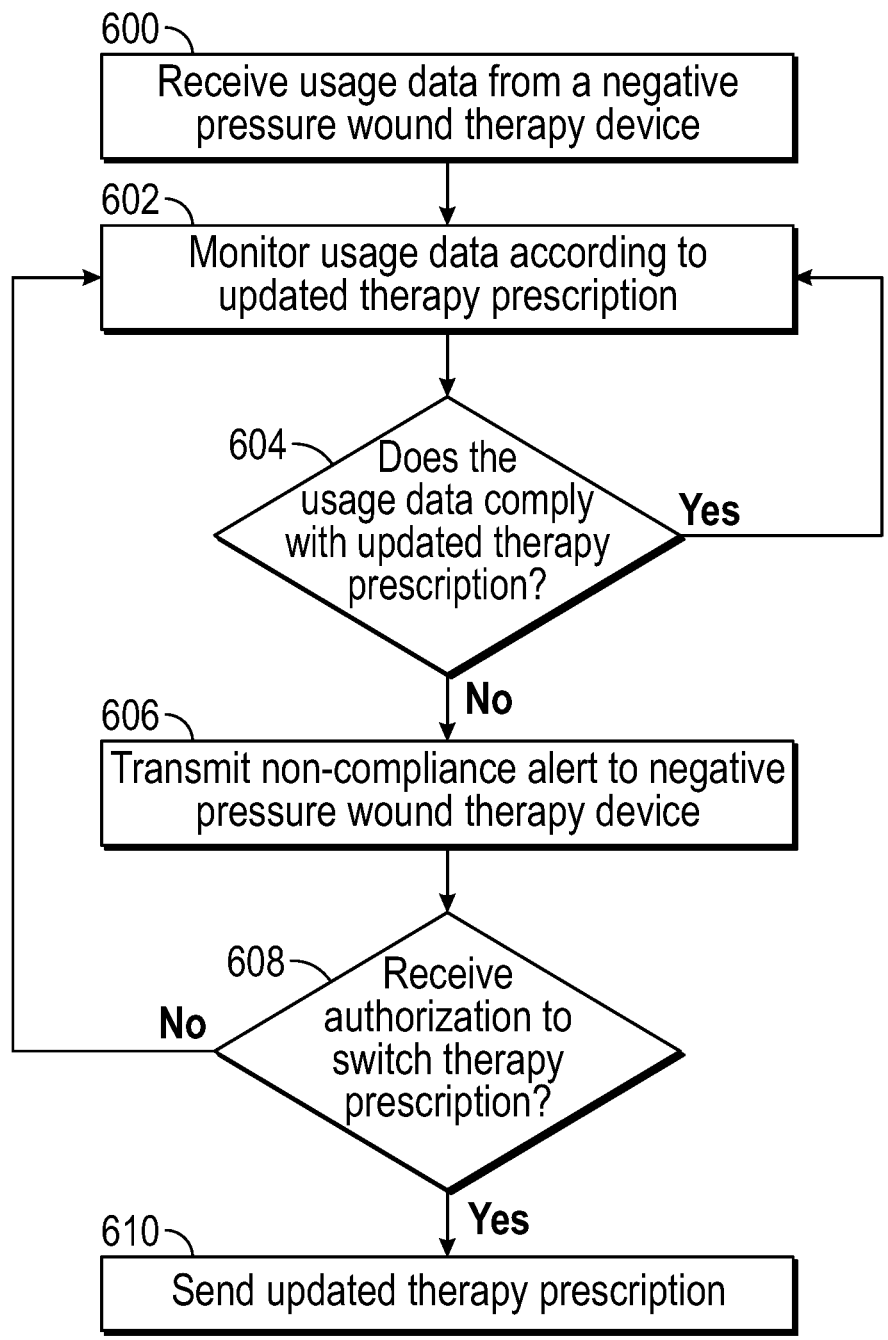
FIG. 6 illustrates a process of updating a therapy prescription.

FIG. 6 illustrates a process of updating a therapy prescription. The illustrated process can be performed by any of the remote computing devices described herein, and in particular by at least one processor of the remote computing device. The process can start in block 600 when the remote computing device receives usage data from the reduced wound therapy device. In some cases, the usage data can include applied pressure over time, amount of exudate in the canister, the amount of time the therapy was applied, and/or the like as described herein. In some cases, the usage data comprises biometric information as described herein. In block 602, the process can verify the received usage data for compliance with an updated therapy prescription. In some cases, the updated therapy prescription has been stored in the remote computing device and has not yet been transmitted to reduced pressure therapy device. In some cases, blocks 600 and 602 can be combined into a single block.

In block 604, the process can determine if the usage data complies with the updated therapy prescription. For example, the process can verify if the usage data matches or exceeds expected usage data associated with the updated therapy prescription (such as, verify if the therapy time matches or exceeds the expected therapy time, verify that applied pressure is within a threshold range, and/or the like). In some cases, the block 604 is executed periodically, such as at regular intervals. In some cases, the block 604 is executed continuously.

If the process determines that the usage data complies with the updated therapy prescription, the process can return to block 602. If the process determines that the usage data does not comply with the updated therapy prescription, the process can proceed to block 606. In block 606, the process can transmit a non-compliance alert to the reduced pressure therapy device. In some cases, the alert can include non-compliance information indicating which one or more parameters of the therapy failed to be compliant. In block 608, the process can determine whether authorization to switch to the updated therapy prescription has been received (for example, from a healthcare provider as described herein). If authorization has not been received, the process can return to block 602. In some cases, the process can alternatively terminate.

If the authorization has been received, the process can transition to block 610 and transmit the updated therapy prescription to the reduced pressure therapy device. In some cases, one or more of the blocks 608 and 610 may not be implemented. For example, the updated therapy prescription can be transmitted in block 606 (or in another block) as described herein.

Other Variations

Although some embodiments describe negative pressure wound therapy, the systems, devices, and/or methods disclosed herein can be applied to other types of therapies usable standalone or in addition to TNP therapy. Systems, devices, and/or methods disclosed herein can be extended to any medical device, and in particular any wound treatment device. For example, systems, devices, and/or methods disclosed herein can be used with devices that provide one or more of ultrasound therapy, oxygen therapy, neurostimulation, microwave therapy, active agents, antibiotics, antimicrobials, or the like. Such devices can, in addition, provide TNP therapy.

Any of transmission of data described herein can be performed securely. For example, one or more of encryption, https protocol, secure VPN connection, error checking, confirmation of deliver can be utilized.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures may be implemented as software and/or firmware on a processor, controller, ASIC, FPGA, and/or dedicated hardware. Furthermore, the features and attributes of the specific embodiments disclosed above may be combined in different ways to form additional embodiments, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Conditional language used herein, such as, among others, "can," "could", "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A negative pressure wound therapy device comprising:
    a negative pressure source configured to be fluidically connected to a dressing positioned over a wound, the negative pressure source further configured to provide a negative pressure therapy to the wound;
    a user interface configured to receive input from a user and provide feedback to the user; and
    a controller configured to:
    receive from the user interface a request to provide the negative pressure therapy in accordance with a default therapy prescription;
    in response to receipt of the request, cause the negative pressure source to provide the negative pressure therapy to the wound in accordance with the default therapy prescription;
    transmit or cause transmission of a usage data associated with provision of the negative pressure therapy over a time duration to a remote computer;
    prior to switching the negative pressure therapy from the default therapy prescription to an updated therapy prescription different from the default therapy prescription, cause the remote computer to monitor, based on the usage data, compliance of the provision of the negative pressure therapy over at least a portion of the time duration with the updated therapy prescription;
    receive an indication from the remote computer that the provision of the negative pressure therapy over at least the portion of the time duration was noncompliant with the updated therapy prescription;
    in response to receipt of the indication:
    provide a non-compliant therapy alert via the user interface;
    provide a prompt on the user interface requesting an authorization to switch a therapy prescription from the default therapy prescription to the updated therapy prescription; and
    cause receipt from the user interface an the authorization to switch the therapy prescription from the default therapy prescription to the updated therapy prescription; and
    in response to receipt of the authorization to switch the therapy prescription from the default therapy prescription to the updated therapy prescription, cause the negative pressure source to provide the negative pressure therapy in accordance with the updated therapy prescription.

2. The device of claim 1, further comprising:
    a primary power source configured to supply power to at least the negative pressure source and the controller; and
    a secondary power source configured to supply power to at least the user interface and the controller,
    wherein the controller is further configured to provide the non-compliant therapy alert via the user interface when the primary power source is disconnected from the controller or depleted.

3. The device of claim 2, wherein the secondary power source is configured to not provide power to the negative pressure source.

4. The device of claim 1, wherein the controller is configured to receive the updated therapy prescription from the remote computer and not cause the negative pressure source to provide the negative pressure therapy in accordance with the updated therapy prescription until receipt of the authorization to switch the therapy prescription from the default therapy prescription to the updated therapy prescription.

5. The device of claim 4, wherein in response to receipt of the updated therapy prescription, the controller is further configured to provide an updated therapy prescription alert via the user interface until receipt of the authorization to switch the therapy prescription from the default therapy prescription to the updated therapy prescription.

6. The device of claim 1, wherein the default therapy prescription and the updated therapy prescription specify at least one of therapy duration, therapy intensity, or therapy mode.

7. The device of claim 6, wherein the usage data includes at least one of therapy duration, therapy intensity, or therapy mode over the time duration.

8. The device of claim 6, wherein the updated therapy prescription specifies at least one of longer therapy duration, higher therapy intensity, or different therapy mode than the default therapy prescription.

9. The device of claim 1, further comprising a housing enclosing the negative pressure source and the controller, wherein the user interface is positioned at least partially on an exterior of the housing.

10. The device of claim 1, wherein:
    the negative pressure therapy is provided to the wound of a patient; and
    the authorization to switch the therapy prescription from the default therapy prescription to the updated therapy prescription is received from a clinician responsive to provision of a password or a biometric check verifying identity of the clinician.

11. The device of claim 1, the controller is configured to cause the remote computer to monitor compliance prior to receiving the updated therapy prescription at the negative pressure wound therapy device.

12. A method of operating a negative pressure wound therapy device, the method comprising, by at least one processor of the device:
    receiving, via a user interface of the device, a request to provide a negative pressure therapy in accordance with a default therapy prescription;
    in response to receiving the request, causing a negative pressure source of the device to provide the negative pressure therapy in accordance with the default therapy prescription;
    transmitting or causing transmission of a usage data associated with provision of the negative pressure therapy over a time duration to a remote computer;
    prior to switching the negative pressure therapy from the default therapy prescription to an updated therapy prescription different from the default therapy prescription, receiving, from the remote computer, an indication that the provision of the negative pressure therapy over at least a portion of the time duration was noncompliant with the updated therapy prescription, the indication being based on the usage data;

in response to receipt of the indication:

generating a non-compliance alert via the user interface of the device;

providing a prompt on the user interface requesting an authorization to switch a therapy prescription from the default therapy prescription to the updated therapy prescription; and obtaining the authorization to switch the therapy prescription from the default therapy prescription to the updated therapy prescription; and in response to obtaining the authorization to switch the therapy prescription from the default therapy prescription to the updated therapy prescription, causing the negative pressure source to provide the negative pressure therapy in accordance with the updated therapy prescription.

13. The method of claim 12, wherein the default therapy prescription specifies at least one of therapy duration, therapy intensity, or therapy mode.

14. The method of claim 12, wherein the usage data includes at least one of therapy duration, therapy intensity, or therapy mode over the time duration.

15. The method of claim 12, wherein the updated therapy prescription specifies at least one of a longer therapy duration, higher therapy intensity, or different therapy mode than the default therapy prescription.

16. The method of claim 12, further comprising configuring the user interface to enable a user to authorize to switch the therapy prescription from the default therapy prescription to the updated therapy prescription.

17. The method of claim 12, further comprising receiving from the remote computer the updated therapy prescription.

\* \* \* \* \*

UNITED STATES PATENT AND TRADEMARK OFFICE
CERTIFICATE OF CORRECTION

PATENT NO. : 11,793,924 B2  
APPLICATION NO. : 17/416385  
DATED : October 24, 2023  
INVENTOR(S) : Hartwell et al.

Page 1 of 1

It is certified that error appears in the above-identified patent and that said Letters Patent is hereby corrected as shown below:

In the Specification

In Column 11, Line 53 (Approx.), delete "shutdown:" and insert --shutdown;--.

In the Claims

In Column 21, Claim 1, Line 52, delete "an" and insert --of--.

Signed and Sealed this  
Twentieth Day of February, 2024

Katherine Kelly Vidal  
*Director of the United States Patent and Trademark Office*